United States Patent
Takahashi et al.

(10) Patent No.: US 11,145,514 B2
(45) Date of Patent: Oct. 12, 2021

(54) REMOVAL LIQUID AND METHOD FOR REMOVING OXIDE OF GROUP III-V ELEMENT, TREATMENT LIQUID FOR TREATING COMPOUND OF GROUP III-V ELEMENT, OXIDATION PREVENTION LIQUID FOR PREVENTING OXIDATION OF GROUP III-V ELEMENT, TREATMENT LIQUID FOR TREATING SEMICONDUCTOR SUBSTRATE, AND METHOD FOR PRODUCING SEMICONDUCTOR SUBSTRATE PRODUCT

(71) Applicant: FUJIFILM Corporation, Tokyo (JP)

(72) Inventors: Satomi Takahashi, Shizuoka (JP); Seongmu Bak, Shizuoka (JP); Atsushi Mizutani, Shizuoka (JP); Tadashi Inaba, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 105 days.

(21) Appl. No.: 15/647,351

(22) Filed: Jul. 12, 2017

(65) Prior Publication Data
US 2017/0309492 A1    Oct. 26, 2017

Related U.S. Application Data

(63) Continuation of application No. PCT/JP2016/053422, filed on Feb. 4, 2016.

(30) Foreign Application Priority Data

Feb. 12, 2015 (JP) ................................ 2015-025478
Feb. 2, 2016 (JP) ................................ 2016-018056

(51) Int. Cl.
*H01L 21/304* (2006.01)
*H01L 21/02* (2006.01)
(Continued)

(52) U.S. Cl.
CPC .......... *H01L 21/304* (2013.01); *C07C 321/04* (2013.01); *C07C 321/22* (2013.01);
(Continued)

(58) Field of Classification Search
CPC ............. H01L 21/304; H01L 21/02057; H01L 21/02052; H01L 21/31111; H01L 21/3081;
(Continued)

(56) References Cited

U.S. PATENT DOCUMENTS 6,200,947 B1 * 3/2001 Takashima ............... C11D 7/06
134/2
7,407,847 B2   8/2008 Doyle et al.
(Continued)

FOREIGN PATENT DOCUMENTS

JP    2-284420 A    11/1990
JP    2000-273663 A    10/2000
(Continued)

OTHER PUBLICATIONS

JPWO2005019499A1 (Year: 2006).*
(Continued)

*Primary Examiner* — Duy Vu N Deo
(74) *Attorney, Agent, or Firm* — Sughrue Mion, PLLC

(57) ABSTRACT

Provided are a removal liquid for removing an oxide of a Group III-V element, an oxidation prevention liquid for preventing the oxidation of an oxide of a Group III-V element or a treatment liquid for treating an oxide of a Group III-V element, each liquid including an acid and a mercapto compound; and a method using each of the same liquids. Further provided are a treatment liquid for treating a semiconductor substrate, including an acid and a mercapto compound, and a method for producing a semiconductor substrate product using the same.

44 Claims, 2 Drawing Sheets

(51) Int. Cl.
*C07D 213/70* (2006.01)
*H01L 21/311* (2006.01)
*C07D 249/12* (2006.01)
*C07D 239/40* (2006.01)
*C07C 323/12* (2006.01)
*C07C 323/52* (2006.01)
*C07C 323/58* (2006.01)
*H01L 21/306* (2006.01)
*C07C 321/04* (2006.01)
*C07C 321/22* (2006.01)
*C07C 321/26* (2006.01)
*C22B 30/04* (2006.01)
*C22B 58/00* (2006.01)
*H01L 21/308* (2006.01)

(52) U.S. Cl.
CPC .......... *C07C 321/26* (2013.01); *C07C 323/12* (2013.01); *C07C 323/52* (2013.01); *C07C 323/58* (2013.01); *C07D 213/70* (2013.01); *C07D 239/40* (2013.01); *C07D 249/12* (2013.01); *C22B 30/04* (2013.01); *C22B 58/00* (2013.01); *H01L 21/02052* (2013.01); *H01L 21/02057* (2013.01); *H01L 21/3081* (2013.01); *H01L 21/30604* (2013.01); *H01L 21/31111* (2013.01); *Y02P 20/582* (2015.11)

(58) Field of Classification Search
CPC ... C07C 323/12; C07C 323/58; C07C 323/52; C07C 321/26; C07C 321/22; C07C 321/04; C07D 213/70; C07D 249/12; C07D 239/40; C22B 58/00; C22B 30/04; Y02P 20/582
See application file for complete search history.

(56) References Cited

U.S. PATENT DOCUMENTS

| | | | | |
|---|---|---|---|---|
| 7,422,793 | B2 * | 9/2008 | Phelps | C23C 22/83 106/14.05 |
| 2006/0134899 | A1 * | 6/2006 | Wu | H01L 29/6653 438/595 |
| 2008/0261847 | A1 * | 10/2008 | Visintin | H01L 21/02079 510/176 |
| 2009/0023231 | A1 | 1/2009 | Ohmi et al. | |

FOREIGN PATENT DOCUMENTS

| | | |
|---|---|---|
| JP | 2004-342733 A | 12/2004 |
| JP | 2009-105299 A | 5/2009 |
| KR | 1020070063356 A | 6/2007 |
| TW | 500831 B | 9/2002 |
| TW | 200511446 A | 3/2005 |
| TW | 200717633 A | 5/2007 |
| WO | 03/060192 A1 | 7/2003 |
| WO | 2006/129538 A1 | 12/2006 |
| WO | 2006/129549 A1 | 12/2006 |
| WO | 2007/088848 A1 | 8/2007 |
| WO | 2013/101907 A1 | 7/2013 |

OTHER PUBLICATIONS

WO2007088848; Semiconductor Device Manufacturing Method and Method for Reducing Microroughness of Semiconductor (Year: 2007).*
NIH, National Library of Medicine, Thioglycolic acid, PubChem 2009-2018.*
Communication dated Jul. 19, 2018 from the Korean Intellectual Property Office in counterpart Korean application No. 10-2017-7021894.
Communication dated Dec. 5, 2017 from the Japanese Patent Office in counterpart application No. 2016-574772.
J.-P. Colinge, "FinFETs and Other Multi-Gate Transistor", Integrated Circuits and Systems, 2008, vol. XV, pp. 1-335.
International Search Report of PCT/JP2016/053422 dated May 10, 2016 [PCT/ISA/210].
Extended European Search Report dated Feb. 8, 2018 issue by the European Patent Office in counterpart European Application No. 16749153.9.
Communication dated Jan. 31, 2019, from Korean Intellectual Property Office in counterpart application No. 10-2017-7021894.
Communication dated May 29, 2019, from the Intellectual Property Office of Taiwan in counterpart application No. 105103962.
First Office Action dated Feb. 3, 2020, from the China National Intellectual Property Administration in Application No. 201680006546.5.
Communication dated Sep. 14, 2020, from the China National Intellectual Property Administration in Application No. 201680006546.5.
Communication dated Jun. 2, 2020, from the Taiwanese Intellectual Property Office in application No. 105103962.
Communication dated Oct. 30, 2020, from the Taiwanese Intellectual Property Office in application No. 105103962.
The Rejection Decision dated May 11, 2021 from the China National Intellectual Property Administration in CN Application No. 201680006546.5.

* cited by examiner

REMOVAL LIQUID AND METHOD FOR REMOVING OXIDE OF GROUP III-V ELEMENT, TREATMENT LIQUID FOR TREATING COMPOUND OF GROUP III-V ELEMENT, OXIDATION PREVENTION LIQUID FOR PREVENTING OXIDATION OF GROUP III-V ELEMENT, TREATMENT LIQUID FOR TREATING SEMICONDUCTOR SUBSTRATE, AND METHOD FOR PRODUCING SEMICONDUCTOR SUBSTRATE PRODUCT

CROSS-REFERENCE TO RELATED APPLICATIONS

This application is a Continuation of PCT International Application No. PCT/JP2016/053422 filed on Feb. 4, 2016, which claims priorities under 35 U.S.C. § 119 (a) to Japanese Patent Application No. JP2015-025478 filed on Feb. 12, 2015, and JP2016-018056 filed on Feb. 2, 2016. Each of the above applications is hereby expressly incorporated by reference, in its entirety, into the present application.

BACKGROUND OF THE INVENTION

1. Field of the Invention

The present invention relates to a removal liquid for removing an oxide of a Group III-V element and a removal method for removing an oxide of a Group III-V element using the same, as well as a treatment liquid for treating a semiconductor substrate. Further, the present invention relates to a treatment liquid for treating a compound of a Group III-V element, an oxidation prevention liquid for preventing the oxidation of a Group III-V element, and a method for producing a semiconductor substrate product.

2. Description of the Related Art

Production of an integrated circuit involves multiple steps of various processing steps. In the production process, deposition, lithography, etching, and the like of a variety of materials are repeated many times. Especially, etching and film removal are important processes. Specific materials need to be selectively removed and other materials need to remain without being corroded. In some cases, it is required to remove only the predetermined layers in a manner that leaves layers of similar metal species or layers of more highly corrosive materials. The size of wirings and integrated circuits in the semiconductor substrate has become increasingly smaller and the importance of precisely removing a film or the like without corroding the member to be left is increasing.

Taking a field effect transistor as an example, along with its rapid miniaturization, there is a strong demand for thinning of a silicide layer formed on the upper surface of a source/drain region and development of a novel material. In addition, various multi-gate transistors (MuFETs) have been proposed in place of a general MOSFET structure (see U.S. Pat. No. 7,407,847B and FinFETs and Other Multi-Gate Transistors, Colinge, J.-P. (Ed.) 2008, XV). For example, transistors having a complex structure such as a Flexfet, a FinFET, a GAAFET, and a tri-gate transistor have been proposed, and development of production techniques suited to these transistors is desired.

SUMMARY OF THE INVENTION

Meanwhile, in the process of producing a semiconductor substrate, members may be subject to oxidation under the condition that the surface of each member is exposed. It is required to remove only the residue of oxide film and oxide to thereby obtain a clean member surface. Further, even when the residue of oxide film and oxide is removed unless the oxidation of the surface exposed after etching or removal of the film is prevented, subsequent electrical properties are adversely affected. Therefore, the importance of preventing oxidation of the etched or film-removed surface is increasing. In the present invention, attention was focused particularly on the removal of an oxide of a Group III-V element and the prevention of oxidation after the removal of an oxide.

An object of the present invention is to provide a removal liquid for removing an oxide of a Group III-V element which is capable of removing an oxide of a Group III-V element and, if necessary, is also capable of suppressing or preventing the elution of a Group III-V element (metal) from the film of the element, and a method for removing an oxide of a Group III-V element using the same, as well as a treatment liquid for treating a semiconductor substrate and a method for producing a semiconductor substrate product.

Another object of the present invention is to provide a treatment liquid for treating a compound of a Group III-V element which is capable of removing an oxide of a Group III-V element and is also capable of suppressing or preventing the oxidation of a Group III-V element after the removal of an oxide and, if necessary, the elution of a Group III-V element (metal) from the film of the element.

Still another object of the present invention is to provide an oxidation prevention liquid for preventing the oxidation of a Group III-V element which is capable of suppressing or preventing the oxidation of a Group III-V element and furthermore, if necessary, is capable of suppressing or preventing the elution of a Group III-V element from the film of the element.

The above-mentioned objects have been achieved by the following means.

[1] A removal liquid for removing an oxide of a Group III-V element, containing an acid and a mercapto compound.

[2] The removal liquid according to [1], in which the mercapto compound has at least one of a carboxyl group or a hydroxyl group, and a thiol group.

[3] The removal liquid according to [1] or [2], in which the mercapto compound has 1 to 12 carbon atoms and one or more and four or less thiol groups within a molecule.

[4] The removal liquid according to any one of [1] to [3], in which the acid is an inorganic acid.

[5] The removal liquid according to [4], in which the inorganic acid is hydrochloric acid.

[6] The removal liquid according to any one of [1] to [5], in which the elution of a Group III-V element is suppressed or prevented and an oxide of a Group III-V element is removed.

[7] The removal liquid according to any one of [1] to [6], in which the Group III-V element is at least one selected from In, Ga, As, and P.

[8] The removal liquid according to any one of [1] to [7], in which the content of the acid is 0.05 mass % or more and 20 mass % or less.

[9] The removal liquid according to any one of [1] to [8], in which the content of the mercapto compound is 0.01 mass % or more and 10 mass % or less.

[10] The removal liquid according to any one of [1] to [9], in which the mercapto compound is represented by any one of the following Formulae (1) to (4).

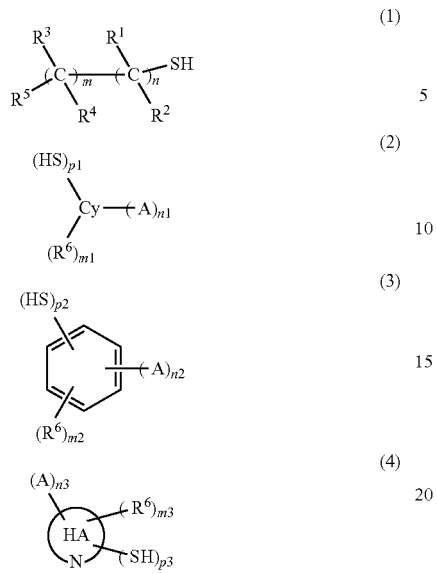

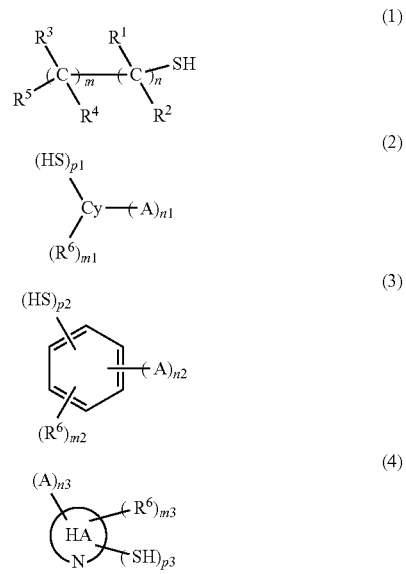

$R^1$ to $R^5$ are each independently a hydrogen atom, a thiol group, a hydroxyl group, a carboxyl group, an alkyl group, an alkenyl group, an aryl group, an aralkyl group, an amino group, an acyl group, or an acylamino group. $R^1$ to $R^5$ may be bonded to one another to form a ring.

m and n are an integer. m+n is an integer of 1 to 12.

One or more of $R^1$ to $R^5$ in a molecule are present as a carboxyl group or a hydroxyl group.

A is a carboxyl group or a hydroxyl group.

Cy is a structure obtained by removing m1+n1+p1 number of hydrogen atoms from a cyclic aliphatic hydrocarbon.

$R^6$ is an alkyl group, an alkenyl group, an aryl group, an aralkyl group, an amino group, an acyl group, or an acylamino group.

n1, n2, p1, and p2 are an integer of 1 to 4 and m1 and m2 are an integer of 0 to 4, provided that n2+m2+p2 is 6 or less.

HA represents a structure obtained by removing m3+n3+p3 number of hydrogen atoms from an N-containing heteroaromatic ring.

n3 and m3 are an integer of 0 to 5. p3 is an integer of 1 to 4.

[11] A treatment liquid for treating a semiconductor substrate, containing an acid and a mercapto compound, in which the mercapto compound has at least one of a carboxyl group or a hydroxyl group, and a thiol group.

[12] A treatment liquid for treating a semiconductor substrate, containing an acid and a mercapto compound, in which the mercapto compound has 1 to 12 carbon atoms and one or more and four or less thiol groups within a molecule.

[13] The treatment liquid according to [11] or [12], in which the acid is an inorganic acid.

[14] The treatment liquid according to [13], in which the inorganic acid is hydrochloric acid.

[15] The treatment liquid according to any one of [11] to [14], in which the content of the acid is 0.05 mass % or more and 20 mass % or less.

[16] The treatment liquid according to any one of [11] to [15], in which the content of the mercapto compound is 0.01 mass % or more and 10 mass % or less.

[17] The treatment liquid according to any one of [11] to [16], in which the mercapto compound is represented by any one of the following Formulae (1) to (4).

[18] A removal method for removing an oxide of a Group III-V element, having:
applying a treatment liquid (removal liquid) containing an acid and a mercapto compound to an oxide of a Group III-V element to remove the oxide of a Group III-V element.

[19] The removal method according to [18], in which the elution of a Group III-V element is suppressed or prevented and an oxide of a Group III-V element is removed.

[20] The removal method according to [18] or [19], in which the treatment is carried out under a condition that light of 500 nm or less is blocked or under a dark room condition.

[21] A method for producing a semiconductor substrate product, having producing a semiconductor substrate product through the removal method according to any one of [18] to [20].

[22] A treatment liquid for treating a compound of a Group III-V element, comprising an acid and a mercapto compound.

[23] The treatment liquid according to [22], in which the mercapto compound contains at least one of a carboxyl group or a hydroxyl group, and a thiol group.

[24] The treatment liquid according to [22], in which the mercapto compound has 1 to 12 carbon atoms and one or more and four or less thiol groups within a molecule. [25] The treatment liquid according to any one of [22] to [24], in which the acid is an inorganic acid.

[26] The treatment liquid according to [25], in which the inorganic acid is hydrochloric acid.

[27] The treatment liquid according to any one of [22] to [26], in which the elution of a Group III-V element is suppressed or prevented and an oxide of a Group III-V element is removed.

[28] The treatment liquid according to any one of [22] to [27], in which the Group III-V element is at least one selected from In, Ga, As, and P.

[29] The treatment liquid according to any one of [22] to [28], in which the content of the acid is 0.05 mass % or more and 20 mass % or less.

[30] The treatment liquid according to any one of [22] to [29], in which the content of the mercapto compound is 0.01 mass % or more and 10 mass % or less.

[31] The treatment liquid according to any one of [22] to [30], in which the mercapto compound is represented by any one of the following Formulae (1) to (4).

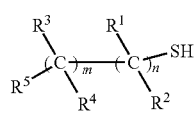
(1)

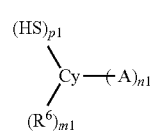
(2)

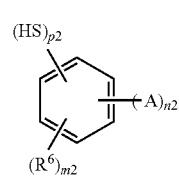
(3)

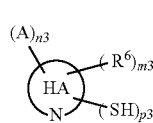
(4)

$R^1$ to $R^5$ are each independently a hydrogen atom, a thiol group, a hydroxyl group, a carboxyl group, an alkyl group, an alkenyl group, an aryl group, an aralkyl group, an amino group, an acyl group, or an acylamino group. $R^1$ to $R^5$ may be bonded to one another to form a ring.

m and n are an integer. m+n is an integer of 1 to 12.

One or more of $R^1$ to $R^5$ in a molecule are present as a carboxyl group or a hydroxyl group.

A is a carboxyl group or a hydroxyl group.

Cy is a structure obtained by removing m1+n1+p1 number of hydrogen atoms from a cyclic aliphatic hydrocarbon.

$R^6$ is an alkyl group, an alkenyl group, an aryl group, an aralkyl group, an amino group, an acyl group, or an acylamino group.

n1, n2, p1, and p2 are an integer of 1 to 4 and m1 and m2 are an integer of 0 to 4, provided that n2+m2+p2 is 6 or less.

HA represents a structure obtained by removing m3+n3+p3 number of hydrogen atoms from an N-containing heteroaromatic ring.

n3 and m3 are an integer of 0 to 5. p3 is an integer of 1 to 4.

[32] An oxidation prevention liquid for preventing the oxidation of a Group III-V element, containing an acid and a mercapto compound.

[33] The oxidation prevention liquid according to [32], in which the mercapto compound has at least one of a carboxyl group or a hydroxyl group, and a thiol group.

[34] The oxidation prevention liquid according to [32], in which the mercapto compound has 1 to 12 carbon atoms and one or more and four or less thiol groups within a molecule.

[35] The oxidation prevention liquid according to any one of [32] to [34], in which the acid is an inorganic acid.

[36] The oxidation prevention liquid according to [35], in which the inorganic acid is hydrochloric acid.

[37] The oxidation prevention liquid according to any one of [32] to [36], in which the elution of a Group III-V element is suppressed or prevented and an oxide of a Group III-V element is removed.

[38] The oxidation prevention liquid according to any one of [32] to [37], in which the Group III-V element is at least one selected from In, Ga, As, and P.

[39] The oxidation prevention liquid according to any one of [32] to [38], in which the content of the acid is 0.05 mass % or more and 20 mass % or less.

[40] The oxidation prevention liquid according to any one of [32] to [39], in which the content of the mercapto compound is 0.01 mass % or more and 10 mass % or less.

[41] The oxidation prevention liquid according to any one of [32] to [40], in which the mercapto compound is represented by any one of the following Formulae (1) to (4).

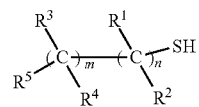
(1)

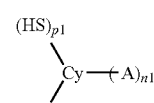
(2)

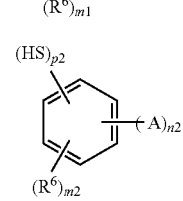
(3)

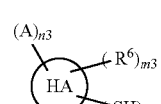
(4)

$R^1$ to $R^5$ are each independently a hydrogen atom, a thiol group, a hydroxyl group, a carboxyl group, an alkyl group, an alkenyl group, an aryl group, an aralkyl group, an amino group, an acyl group, or an acylamino group. $R^1$ to $R^5$ may be bonded to one another to form a ring.

m and n are an integer. m+n is an integer of 1 to 12.

One or more of $R^1$ to $R^5$ in a molecule are present as a carboxyl group or a hydroxyl group.

A is a carboxyl group or a hydroxyl group.

Cy is a structure obtained by removing m1+n1+p1 number of hydrogen atoms from a cyclic aliphatic hydrocarbon.

$R^6$ is an alkyl group, an alkenyl group, an aryl group, an aralkyl group, an amino group, an acyl group, or an acylamino group.

n1, n2, p1, and p2 are an integer of 1 to 4 and m1 and m2 are an integer of 0 to 4, provided that n2+m2+p2 is 6 or less.

HA represents an N-containing heteroaromatic ring. n3 and m3 are an integer of 0 to 5. p3 is an integer of 1 to 4.

The Group III-V element in the present specification is a generic name for an element belonging to Group IIIb (Group 13) of the periodic table and an element belonging to Group Vb (Group 15) of the periodic table. Preferred is In, Ga, P, As, Al, Sb, Tl, or Bi, and more preferred is In, Ga, As, or P.

According to the present invention, it is possible to remove an oxide of a Group III-V element and, if necessary, it is possible to suppress or prevent the elution of a Group III-V element from the film of the element.

Further, according to the present invention, it is possible to suppress or prevent the oxidation of a Group III-V element and, if necessary, it is possible to suppress or prevent the elution of a Group III-V element from the film of the element.

Further, according to the present invention, it is possible to remove an oxide of a Group III-V element and, if necessary, it is possible to suppress or prevent the elution of Group III-V element from the film of the element, and it is further possible to suppress or prevent the oxidation of a Group III-V element after the removal of an oxide.

The above and other features and advantages of the present invention will become more apparent from the following descriptions, with reference to the accompanying drawings as appropriate.

DESCRIPTION OF THE PREFERRED EMBODIMENTS

Figure 1:
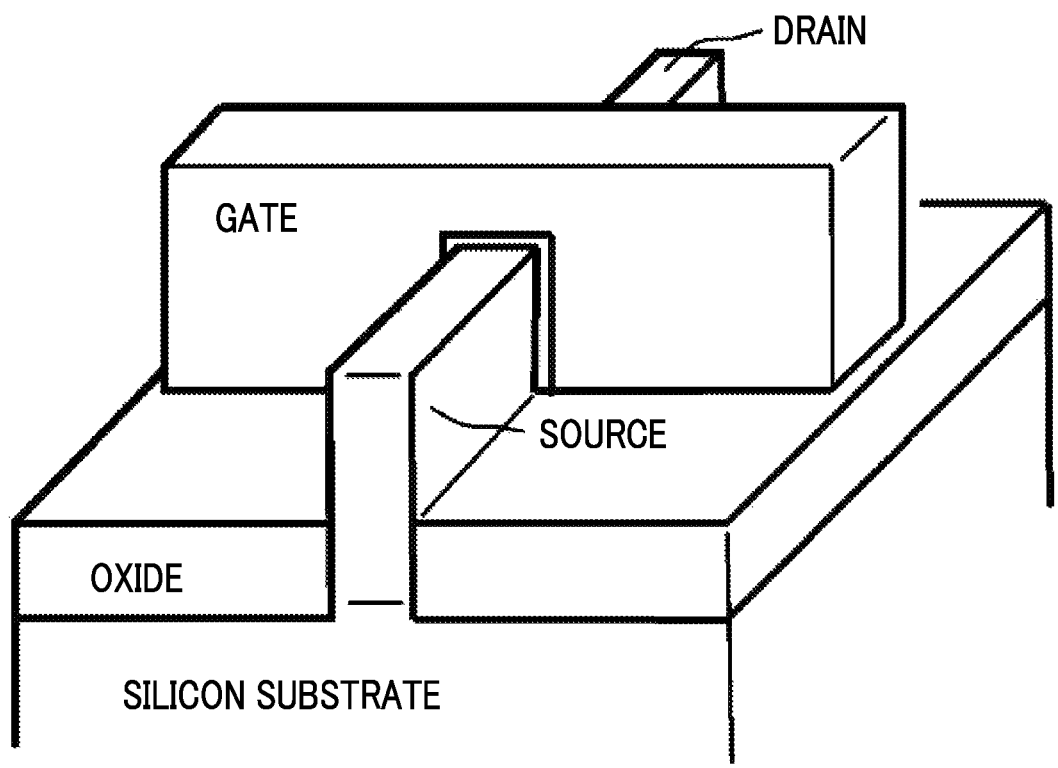
FIG. 1 is a perspective view schematically showing a structure of a FinFET.

In the description of the present invention, when a group (atomic group) is denoted without specifying whether substituted or unsubstituted, the group is intended to include both of a group having no substituent and a group having a substituent, within a range not impairing the effects of the present invention. For example, an "alkyl group" includes not only an alkyl group having no substituent (unsubstituted alkyl group) but also an alkyl group having a substituent (substituted alkyl group). This shall also apply to respective compounds.

Further, the term "preparation" as used herein is intended to include the provision of a specific material by synthesis or formulation thereof, but also the procurement of a predetermined material by purchase or the like.

Further, in the present invention, 1 Å (angstrom) corresponds to 0.1 nm.

The treatment liquid for treating a compound of a Group III-V element according to the present invention, the oxidation prevention liquid for preventing the oxidation of a Group III-V element according to the present invention, the removal liquid for removing an oxide of a Group III-V element according to the present invention, and the treatment liquid for treating a semiconductor substrate according to the present invention each contain an acid and a mercapto compound. Therefore, these liquids are also collectively referred to as a liquid containing an acid and a mercapto compound according to the present invention (simply a liquid of the present invention).

The treatment liquid for treating a compound of a Group III-V element according to the present invention, the oxidation prevention liquid for preventing the oxidation of a Group III-V element according to the present invention, and the removal liquid for removing an oxide of a Group III-V element according to the present invention are respectively referred to as a compound treatment liquid, an oxidation prevention liquid, and a removal liquid, focusing on their action and function. That is, in the case of paying attention to the action and function of removing an oxide of a Group III-V element and suppressing or preventing the oxidation of a Group III-V element after the removal of an oxide, it is referred to as a compound treatment liquid. In the case of paying attention to the action and function of removing an oxide of a Group III-V element, it is referred to as a removal liquid. In the case of paying attention to the action and function of suppressing or preventing the oxidation of a Group III-V element, it is referred to as an oxidation prevention liquid.

Further, the treatment liquid for treating a semiconductor substrate according to the present invention is suitably applied to a compound of a Group III-V element present in the semiconductor substrate.

Therefore, all of the liquids of the present invention are the same in composition, preferred form, a container for storage or transport, usage form (for example, a kit or concentrated liquid), preparation method and the like, which are described in detail below.

In the present invention, examples of the compound of a Group III-V element to which the compound treatment liquid is applied include compounds containing at least one of Group III elements and at least one of Group V elements, including Group III-V elements (metals), and oxides of Group III-V elements. Here, the Group III-V element (metal) may be a mixture (aggregate) of a Group III element (elemental substance) and a Group V element (elemental substance), as is apparent from the description of the present invention to be described later, and is meant to include Group III-V semiconductors and the like showing semiconductivity. The Group III-V semiconductor is a compound semiconductor containing at least one of Group III elements and at least one of Group V elements, examples of which include GaAs, InP, InAs, InGaAs, InAlAs, and GaAsP. Among them, preferred is InGaAs or InP.

In the present invention, the Group III-V element to which the oxidation prevention liquid is applied is meant to include Group III-V semiconductors, as described above.

The oxide of a Group III-V element to which the removal liquid is applied includes oxides of the above-mentioned Group III-V semiconductor. Specific examples of the oxide include oxides of the above-mentioned Group III-V semiconductor, among which preferred is an oxide of InGaAs or InP.

Further, the semiconductor substrate to which the treatment liquid for treating a semiconductor substrate is applied is not particularly limited as long as it is a semiconductor substrate in which the above-mentioned compound of a Group III-V element is present. Such a semiconductor substrate will be described in detail later.

The above-mentioned Group III-V element and oxides and compounds thereof are not limited in their forms and may be in a film, a particle or a bulky form.

The liquid of the present invention contains an acid and a mercapto compound.

The liquid of the present invention will be described in detail, but the following matters are applicable to any of the liquids of the present invention.

Hereinafter, the preferred embodiments thereof will also be described in detail with reference to the accompanying drawings.

[Liquid of Present Invention]

The liquid of the present invention contains an acid and a mercapto compound as described above, but may also contain other components. Here, the mercapto compound is a generic term for compounds having a thiol group within the molecule. Optional components that are further included may be, for example, water and an organic solvent. In particular, it is preferred that the liquid of the present invention substantially consists of only (i) an acid, a mercapto compound, and water, substantially consists of only (ii) an acid, a mercapto compound, and an organic solvent, or substantially consists of only (iii) an acid, a mercapto compound, water, and an organic solvent. Here, the term "substantially" means that inevitable impurities or trace amounts of additive components may be contained within the range that the effect of the present invention is exerted. Individual components will be described below.

(Acid)

Examples of the acid include inorganic acids such as halogen acid (hydrochloric acid (HCl), hydrofluoric acid (HF), hydrobromic acid (HBr), or the like), sulfuric acid ($H_2SO_4$), nitric acid ($HNO_3$), phosphoric acid ($H_3PO_4$), and phosphonic acid ($H_3PO_3$), and various organic acids. In particular, in the present invention, an inorganic acid is preferable, halogen acid is more preferable, hydrochloric acid or hydrobromic acid is still more preferable, and hydrochloric acid is particularly preferable. These acids may be used alone or in combination of two or more thereof.

The concentration of the acid in the liquid of the present invention is preferably 0.05 mass % or more, more preferably 0.1 mass % or more, and particularly preferably 1 mass % or more. The upper limit is preferably 20 mass % or less, more preferably 10 mass % or less, and particularly preferably 5 mass % or less. It is preferred the acid is applied within a range of the above-specified concentration because effective protection can be achieved for a Group III-V element (metal) while achieving good performance with respect to the removal of an oxide of a Group III-V element. Still more specifically, including the estimation, it is understood that the acid is responsible for dissolving an oxide, but solubility of the oxide is understood to be increased by further using a mercapto compound. If the concentration of the acid is too high, dissolution of the metal (Group III-V element) becomes excessive, making it difficult to give high selectivity.

(Mercapto Compound)

The mercapto compound preferably contains at least one of a carboxyl group or a hydroxyl group, and a thiol group (sulfanyl group: —SH). Alternatively, the mercapto compound preferably has 1 to 12 carbon atoms (preferably 1 to 6) and one or more and four or less (preferably two or less) thiol groups within the molecule. The mercapto compound is more preferably represented by any one of the following Formulae (1) to (4).

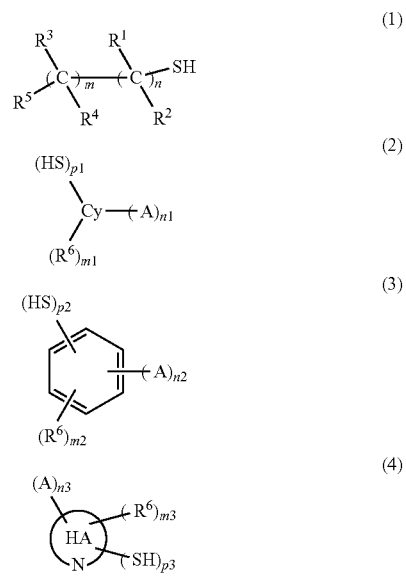

$R^1$ to $R^5$ are each independently a hydrogen atom, a thiol group, a hydroxyl group, a carboxyl group, an alkyl group (preferably having 1 to 12 carbon atoms, more preferably having 1 to 6 carbon atoms, and particularly preferably having 1 to 3 carbon atoms), an alkenyl group (preferably having 2 to 12 carbon atoms and more preferably having 2 to 6 carbon atoms), an aryl group (preferably having 6 to 22 carbon atoms, more preferably having 6 to 14 carbon atoms, and particularly preferably having 6 to 10 carbon atoms), an aralkyl group (preferably having 7 to 23 carbon atoms, more preferably having 7 to 15 carbon atoms, and particularly preferably having 7 to 11 carbon atoms), an amino group ($NR^N_2$: $R^N$ is a hydrogen atom, an alkyl group having 1 to 3 carbon atoms, or an aryl group having 6 to 14 carbon atoms), an acyl group (preferably having 2 to 12 carbon atoms and more preferably having 2 to 6 carbon atoms), or an acylamino group (preferably having 2 to 12 carbon atoms and more preferably having 2 to 6 carbon atoms).

m and n are an integer. m+n is an integer of 1 to 12, preferably 1 to 8, more preferably 1 to 4, and still more preferably 2 to 4.

It is a condition that one or more of $R^1$ to $R^5$ in the molecule are present as a carboxyl group or a hydroxyl group, and it is preferred that one or more and four or less of $R^1$ to $R^5$ are present as a carboxyl group or a hydroxyl group.

$R^1$ to $R^5$ may be bonded to one another to form a ring, provided that the compound in which $R^1$ to $R^5$ are bonded to one another to form a ring is different from the compound represented by the above-mentioned Formula (2).

A is a carboxyl group or a hydroxyl group.

Cy is a structure obtained by removing m1+n1+p1 number of hydrogen atoms from a cyclic aliphatic hydrocarbon. Examples of the cyclic aliphatic hydrocarbon include cyclohexane, cyclopentane, adamantane, and norbornane.

$R^6$ is an alkyl group (preferably having 1 to 12 carbon atoms, more preferably having 1 to 6 carbon atoms, and particularly preferably having 1 to 3 carbon atoms), an alkenyl group (preferably having 2 to 12 carbon atoms and more preferably having 2 to 6 carbon atoms), an aryl group (preferably having 6 to 22 carbon atoms, more preferably having 6 to 14 carbon atoms, and particularly preferably having 6 to 10 carbon atoms), an aralkyl group (preferably having 7 to 23 carbon atoms, more preferably having 7 to 15 carbon atoms, and particularly preferably having 7 to 11 carbon atoms), an amino group ($NR^N{}_2$), an acyl group (preferably having 2 to 12 carbon atoms and more preferably having carbon atoms 2 to 6), or an acylamino group (preferably having 2 to 12 carbon atoms and more preferably having 2 to 6 carbon atoms).

Each of n1, n2, p1, and p2 is an integer of 1 to 4 and each of m1 and m2 is an integer of 0 to 4, provided that n2+m2+p2 is 6 or less.

HA represents a ring structure obtained by removing m3+n3+p3 number of hydrogen atoms from an N-containing heteroaromatic ring in Formula (4). The heteroaromatic ring is not particularly limited as long as it is a ring having at least one nitrogen atom as a ring-constituting atom, which may be a monocyclic or fused ring. Examples of the ring-constituting atom include a carbon atom, an oxygen atom, a sulfur atom, a silicon atom, a selenium atom, and a phosphorus atom, in addition to a nitrogen atom. The heteroaromatic ring is preferably a monocyclic ring which is preferably 5-membered or 6-membered. Examples of the heteroaromatic ring include a 5-membered ring such as a pyrazole ring, an imidazole ring, a triazole ring, an oxazole ring, or a thiazole ring, a 6-membered ring such as a pyridine ring, a pyrimidine ring, a pyrazine ring, a pyridazine ring, a triazine ring, or a tetrazine ring, and a fused ring such as a benzimidazole ring, a benzotriazole ring, a benzoxazole ring, a benzothiazole ring, a quinoline ring, or an isoquinoline ring. Among them, preferred is a pyridine ring, a pyrimidine ring, or a triazole ring and more preferred is a pyridine ring.

In the compound represented by Formula (4), a thiol group is preferably bonded to the ring-constituting atom bonded to the ring-constituting nitrogen atom (2-position with respect to the ring-constituting nitrogen atom). That is, in the case where the compound represented by Formula (4) has one nitrogen atom as a ring-constituting atom, a thiol group is preferably bonded to a ring-constituting atom bonded to the ring-constituting nitrogen atom. Further, in the case where the above-mentioned compound has two or more nitrogen atoms as a ring-constituting atom, a thiol group is preferably bonded to a ring-constituting atom (preferably, a ring-constituting carbon atom) interposed between the ring-constituting nitrogen atom and the ring-constituting carbon atom.

Each of n3 and m3 is an integer of 0 to 5. p3 is an integer of 1 to 4. n3+m3+p3 is preferably 6 or less.

The mercapto compounds may be used alone or in combination of two or more thereof.

Specific examples of the mercapto compound are shown below, but the present invention should not be construed as being limited thereto.

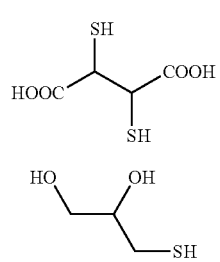

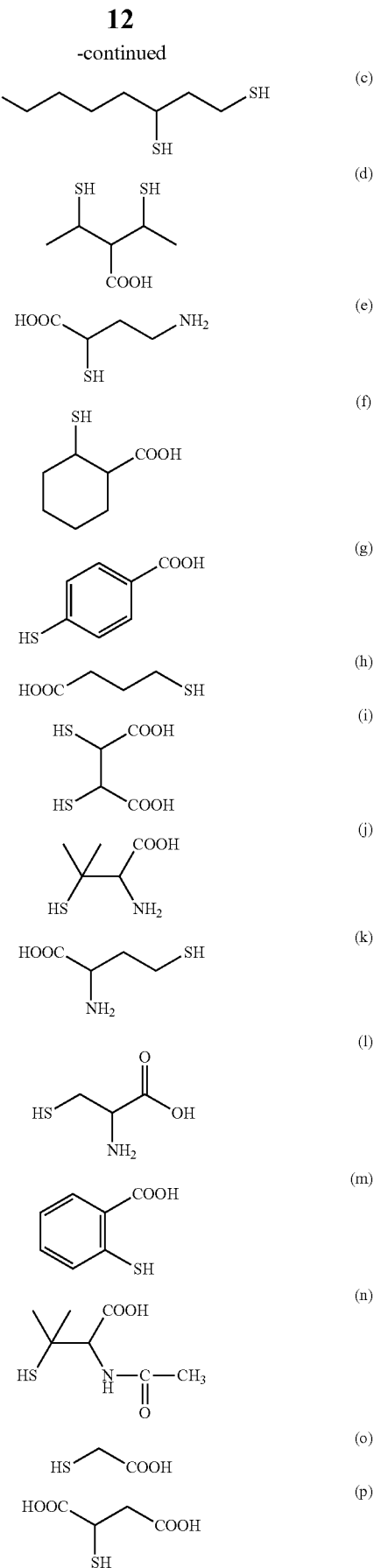

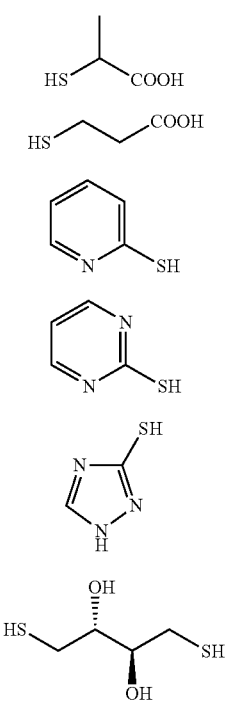

With respect to the liquid of the present invention, the concentration of the mercapto compound in the liquid of the present invention is preferably 10 mass % or less, more preferably 7 mass % or less, still more preferably 5 mass % or less, and particularly preferably 3 mass % or less. The lower limit is preferably 0.01 mass % or more, more preferably 0.05 mass % or more, still more preferably 0.1 mass % or more, and particularly preferably 0.5 mass % or more.

The amount of mercapto compound with respect to 100 parts by mass of the acid is preferably 0.1 parts by mass or more, more preferably 1 part by mass or more, and particularly preferably 5 parts by mass or more. The upper limit is preferably 200 parts by mass or less, more preferably 100 parts by mass or less, and particularly preferably 50 parts by mass or less.

If the amount of the mercapto compound is too small, the effect is not sufficiently exhibited. On the contrary, if the amount of the mercapto compound is too much, there may be a problem in solubility or the mercapto compound may adhere to the entire surface of the oxide film (oxide), so that the dissolution rate of the oxide decreases.

In the liquid of the present invention, the content ratio (mass ratio) between the content of the mercapto compound and the content of the acid is preferably adjusted to the following range. That is, the ratio of the content of the mercapto compound to the content of the acid [content of mercapto compound/content of acid] is preferably 0.001 to 500, more preferably 0.01 to 400 from the viewpoint of improving an oxide film removal rate, and particularly preferably 0.03 to 300 from the viewpoint of inhibiting metal elution.

Specifically, the lower limit of the ratio of content is preferably 0.001 or more, more preferably 0.01 or more from the viewpoint of inhibiting metal elution, and particularly preferably 0.3 or more from the viewpoint of achieving both excellent oxide film removal rate and significant effect.

On the other hand, the upper limit is preferably less than 200, more preferably less than 150 from the viewpoint of inhibiting metal elution, and particularly preferably less than 100 from the viewpoint of achieving both excellent oxide film removal rate and significant effect.

According to the present studies, it has been confirmed that, by adjusting the content ratio in this manner, the liquid of the present invention can favorably maintain the effects of the present invention as described above even after the lapse of time and can also bring about superior recyclability.

Recycling refers to a mode in which the liquid of the present invention is not discarded after one use, for example, the liquid used in any one of treatments of the present invention is used again for any one of the treatments of the present invention. For example, there is an embodiment in which the liquid once used for treating a semiconductor substrate is used again for treating a semiconductor substrate.

At the time of recycling, when washing is repeated, trace amount elution of a Group III-V element or the material used for other semiconductors into the treatment liquid occurs. Although the effect of the present invention may be changed by accumulation thereof, it has been found that when the content ratio is within the above-specified range, recyclability is excellent. This is presumed to be due to the fact that the acid and the mercapto compound interact with each other.

Therefore, the liquid of the present invention can be recycled and used.

(Organic Solvent)

Examples of the organic solvent include an aliphatic compound, a halogenated hydrocarbon compound, an alcohol compound, an ether compound, an ester compound, a ketone compound, a nitrile compound, an amide compound, a sulfoxide compound, and an aromatic compound. These organic solvents may be mixed and used. Examples of each solvent compound are given below.

Aliphatic compound:
hexane, heptane, cyclohexane, methylcyclohexane, octane, pentane, cyclopentane, or the like Halogenated hydrocarbon compound:
methylene chloride, chloroform, dichloromethane, ethane dichloride, carbon tetrachloride, trichloroethylene, tetrachloroethylene, epichlorohydrin, monochlorobenzene, o-dichlorobenzene, allyl chloride, HCFC, methyl monochloroacetate, ethyl monochloroacetate, monochloroacetic acid, trichloroacetic acid, methyl bromide, methyl iodide, tri(tetra)chloroethylene, or the like Alcohol compound:
methanol, ethanol, 1-propanol, 2-propanol, 2-butanol, ethylene glycol, propylene glycol, glycerin, 1,6-hexanediol, cyclohexanediol, sorbitol, xylitol, 2-methyl-2,4-pentanediol, 1,3-butanediol, 1,4-butanediol, or the like Ether compound (including a hydroxyl group-containing ether compound):
dimethyl ether, diethyl ether, diisopropyl ether, dibutyl ether, t-butylmethyl ether, cyclohexylmethyl ether, anisole, tetrahydrofuran, alkylene glycol alkyl ether (ethylene glycol monomethyl ether, ethylene glycol monobutyl ether, diethylene glycol, dipropylene glycol, propylene glycol monomethyl ether, diethylene glycol monomethyl ether, triethylene glycol, polyethylene glycol, propylene glycol monomethyl ether, dipropylene glycol monomethyl ether, tripropylene glycol monomethyl ether, or the like), or the like Ester compound:
ethyl acetate, ethyl lactate, 2-(1-methoxy)propylacetate, propylene glycol 1-monomethyl ether 2-acetate, or the like
Ketone compound:
acetone, methyl ethyl ketone, methyl isobutyl ketone, cyclohexanone, 2-heptanone, or the like
Nitrile compound:
acetonitrile, or the like
Amide compound:
N,N-dimethylformamide, 1-methyl-2-pyrrolidone, 2-pyrrolidinone, 1,3-dimethyl-2-imidazolidinone, ε-caprolactam, formamide, N-methylformamide, acetamide, N-methylacetamide, N,N-dimethylacetamide, N-methylpropanamide, hexamethylphosphoric triamide, or the like
Sulfoxide compound:
dimethylsulfoxide, or the like
Aromatic compound:
benzene, toluene, or the like As the organic solvent, it is preferable to use a solvent of a grade in which impurities and coarse particles to be described below are reduced or a solvent which is further purified. The purification method is not particularly limited, but preferred is a purification using a filtration membrane or an ion-exchange membrane or a purification by means of distillation.

The amount of the organic solvent used is not particularly limited, but it is preferably 5 mass % or more and more preferably 7 mass % or more in the liquid of the present invention. The upper limit is preferably 90 mass % or less and more preferably 85 mass % or less.

The above-mentioned organic solvents may be used alone or in combination of two or more thereof.

In the present specification, in the case of identifying a compound or a compound at the end with an acid or the like, it means that, in addition to the corresponding compound, its ions and salts are included within a range of where the effect of the present invention is achieved. Further, similarly, it is meant to include derivatives thereof.

(Water)

The liquid of the present invention preferably contains water (aqueous medium). As the water (aqueous medium), it may be an aqueous medium containing a dissolving component as long as the effect of the present invention is not impaired, or it may contain inevitable traces of mixed components. Among them, preferred is water subjected to a purification treatment such as distilled water, ion exchange water, or ultrapure water. It is particularly preferable to use ultrapure water used for the semiconductor production, and it is most preferable to use water obtained by subjecting such ultrapure water to a further purification to reduce inorganic anions or metal ions. The purification method is not particularly limited, but it is preferably a purification using a filtration membrane or an ion-exchange membrane, or a purification by means of distillation.

The concentration of water is not particularly limited, but it is preferably 50 mass % or more, more preferably 60 mass % or more, and particularly preferably 70 mass % or more in the liquid of the present invention. The upper limit is preferably 99 mass % or less, more preferably 95 mass % or less, and particularly preferably 90 mass % or less.

(Surfactant)

The liquid of the present invention may contain a surfactant. The surfactant is not particularly limited. An anionic surfactant, a cationic surfactant, a nonionic surfactant, a surfactant made of a polymer compound, a fluorine-based surfactant, a polyoxyalkylene-based surfactant, or the like may be appropriately applied.

The concentration of the surfactant is preferably 10 mass % or less, more preferably 5 mass % or less, and still more preferably 1 mass % or less, with respect to the total amount of the liquid of the present invention. The lower limit value is preferably 0.001 mass % or more and more preferably 0.005 mass % or more. The surfactants may be used alone or in combination of two or more thereof.

(Organic Acid)

The liquid of the present invention may contain an organic acid, in addition to the above-mentioned acid. The organic acid is preferably a monofunctional, difunctional, trifunctional, or tetrafunctional organic acid. When the liquid of the present invention contains an organic acid, it is possible to prevent the corrosion of a semiconductor material or/and an insulating film used in a device or the like to which the liquid of the present invention is applied.

Among the organic acids, preferred is carboxylic acid because it effectively prevents the metal corrosion of aluminum, copper, and alloys thereof, and more preferred is hydroxycarboxylic acid having a hydroxy group because it is particularly effective in preventing the corrosion of metals. The carboxylic acid has a chelating effect on these metals. A preferred carboxylic acid includes a monocarboxylic acid and a polycarboxylic acid. Examples of the carboxylic acid include, but are not limited to, formic acid, acetic acid, propionic acid, valeric acid, isovaleric acid, oxalic acid, malonic acid, succinic acid, glutaric acid, maleic acid, fumaric acid, phthalic acid, 1,2,3-benzenetricarboxylic acid, glycolic acid, lactic acid, citric acid, salicylic acid, tartaric acid, gluconic acid, diglycolic acid, malic acid, acetohydroxamic acid, benzohydroxamic acid, salicylhydroxamic acid, phthalhydroxamic acid, benzoic acid, and dihydroxybenzoic acid. Among them, citric acid, malic acid, tartaric acid, glycolic acid, gluconic acid, or lactic acid, which is a hydroxycarboxylic acid, may be preferably used.

It is preferable that the carboxylic acid is formed only from atoms of carbon, hydrogen, and oxygen as constituent elements, and it is more preferable that the carboxylic acid does not have an amino group. These organic acids may be used alone or in combination of two or more thereof. From the viewpoint of effectively preventing metal corrosion, it is preferable to use two or more types of organic acids in combination.

The content of the organic acid is preferably about 0.001 to about 20.0 mass %, more preferably about 0.01 to about 20.0 mass %, and still more preferably 0.01 to 10.0 mass %, with respect to the total mass of the liquid of the present invention.

(pH Adjusting Agent)

In the liquid of the present invention, a pH adjusting agent may be used. Examples of the pH adjusting agent include a pH adjusting agent used for raising the pH of the liquid of the present invention and a pH adjusting agent used for lowering the pH of the liquid of the present invention.

The pH adjusting agent for raising the pH of the liquid of the present invention is not particularly limited as long as it does not inhibit the effect of the liquid of the present invention. Examples thereof include ammonia ($NH_3$), an alkali hydroxide (metal hydroxide) such as sodium hydroxide (NaOH) or potassium hydroxide (KOH), an alkaline earth salt, an amine compound such as isopropylamine, tertiary butylamine, 2-aminoethanol, guanidine, or 1-amino-2-propanol, a hydroxylamine compound such as hydroxylamine, and an alkylammonium hydroxide such as tetramethylammonium hydroxide (TMAH), tetraethylammonium hydroxide, or tetrapropylammonium hydroxide.

The pH adjusting agent for lowering the pH of the liquid of the present invention is not particularly limited as long as it does not inhibit the effect of the liquid of the present invention. Examples thereof include the above-mentioned acids and the above-mentioned organic acids.

The amount of the pH adjusting agent used is not particularly limited. The pH adjusting agent may be used in an amount necessary to adjust the pH to the above-specified range. The pH adjusting agents may be used alone or in combination of two or more thereof.

(Other Components)

In the liquid of the present invention, a corrosion inhibitor ([0132] in JP2014-232874A, [0015] to [0022] in JP2014-185332A, and [0030] to [0037] in JP2014-220300A), a chelating agent ([0024] in JP2014-093407A and [0024] in JP2014-041260A), a pH buffering agent, or an anti-foaming agent may also be suitably used.

(pH)

The pH of the liquid of the present invention is preferably −2 or more, more preferably −1 or more, and particularly preferably 0 or more. The upper limit is preferably 4 or less, more preferably 3 or less, and particularly preferably 2 or less. Setting the pH within this range makes it possible to control the removal rate of oxides, which is thus preferable. The pH is a value measured using F-51 (trade name) manufactured by HORIBA Ltd. at room temperature (25° C.) unless otherwise specified.

(Kit)

The liquid of the present invention may be constituted as a kit in which the raw materials thereof are divided into multiple parts. The kit may be, for example, an embodiment in which, as a first liquid, a liquid composition in which the above-mentioned acid is contained in an aqueous medium is prepared, and, as a second liquid, a liquid composition in which the above-mentioned mercapto compound is contained in an aqueous medium is prepared. As an example of the use thereof, preferred is an embodiment in which both liquids are mixed to prepare the liquid of the present invention, and after that, the liquid is applied to the above-mentioned treatment on a timely basis. An organic solvent or the like may be contained in either thereof. This avoids the deterioration of the liquid performance due to decomposition of the mercapto compound whereby a desired action can be effectively exhibited. The concentration of the acid in the first liquid and the concentration of the mercapto compound in the second liquid can be appropriately set in terms of the concentration after mixing on the basis of the blending amount of the aforementioned one-liquid type.

(Concentrated Liquid)

The liquid of the present invention may be prepared as a concentrated liquid. In this case, it can be used by being diluted with water at the time of use.

(Impurities and Coarse Particles)

In view of the intended use of the liquid of the present invention, it is preferable that impurities in the liquid, for example, a metal component and the like are small. Examples of the metal component include metal elements such as Na, K, Ca, Cu, Mg, Mn, Li, Al, Cr, Ni, Fe, Co, and Zn, the content of which is preferably less than 1 ppm from the viewpoint of suppressing the performance failure of a semiconductor substrate product. In particular, it is preferable that Na, K and Ca ion concentrations in the liquid are each in a range of less than 1 ppb (on a mass basis).

The method for reducing Na, K and Ca ion concentrations in the liquid of the present invention may be, for example, a method of carrying out distillation or filtration using an ion exchange resin in at least one step of a step before mixing the raw materials used in the preparation of the liquid of the present invention and a step after preparing the liquid of the present invention. Another method may be, for example, a method of using a container having less elution of impurities, as will be described later, as the "container" for accommodating the raw materials used in the preparation of the liquid of the present invention. A further method may be, for example, a method of lining the inner wall of a pipe with a fluorine-based resin, so that metal components such as Na, K, or Ca are not eluted from the pipe used at the time of preparing or transporting the liquid of the present invention.

In the liquid of the present invention, the number of coarse particles having an average particle diameter of 0.5 μm or more is preferably in a range of 100 particles/cm$^3$ or less and more preferably in a range of 50 particles/cm$^3$ or less. The term "coarse particles" refers to particles such as grit, dust, organic solids or inorganic solids contained as impurities in the raw material of the liquid of the present invention, and particles such as grit, dust, organic solids or inorganic solids being brought as contaminants during preparation of the liquid of the present invention, which are finally present as particles without being dissolved in the liquid of the present invention. The number of coarse particles present in the liquid of the present invention can be measured in a liquid phase by using a commercially available measuring device in a light scattering type in-liquid particle measuring method using a laser as a light source.

(Filtering)

The liquid of the present invention is preferably filtered with a filter (filtering) for the purpose of controlling the number of foreign materials or coarse particles or reducing defects. Any filter may be used without particular limitation as long as it is conventionally used for filtration or the like. For example, the filter may be a filter formed of a fluororesin such as polytetrafluoroethylene (PTFE), a polyamide-based resin such as nylon, a polyolefin resin such as polyethylene or polypropylene (PP) (including ones having a high density and an ultra-high molecular weight), or the like. Among these materials, preferred are polypropylene (including high-density polypropylene) and nylon. The pore size of the filter is suitably about 0.001 to 1.0 preferably about 0.01 to 0.5 and more preferably about 0.02 to 0.1 By specifying the pore size of the filter to be within this range, it becomes possible to control the number of fine foreign materials such as impurities or aggregates contained in the liquid of the present invention, while suppressing filtration clogging.

In the case of a filter being used, different filters may be used in combination. In that case, filtering by a first filter may be carried out only once or two or more times. In a case of filtering two or more times by combining different filters, the pore size for the second or subsequent filtering is preferably made larger than or equal to that for the first filtering. In addition, first filters having a different pore size in the above-mentioned range may be used in combination. The pore size herein can be set by referring to nominal values of filter manufacturers. Commercially available filters can be selected from various filters supplied by, for example, Nihon Pall Ltd., Advantec Toyo Kaisha, Ltd., Nihon Entegris K.K. (formerly Nihon Mykrolis K.K.) or Kitz Micro Filter Corporation. As the second filter, it is possible to use a filter formed of the same material as the above-mentioned first filter. The pore size of the second filter is suitably about 0.01 to 1.0 μm and preferably about 0.1 to 0.5 μm. Within this range, in the case where component particles are contained in the liquid of the present invention, the number of foreign materials incorporated in the liquid of the present invention can be controlled while these component particles remain. For example, filtering in the first filter is carried out with a mixed liquid containing a part of the components of the liquid of the present invention, and the remaining components are mixed with the filtered mixed liquid to prepare the liquid of the present invention which may be then subjected to second filtering.

(Container)

The liquid of the present invention (irrespective of whether or not it is a kit) can be stored, transported, and used by charging into an arbitrary container as long as it does not cause a problem associated with corrosion or the like. In addition, as a container for storing or transporting the liquid of the present invention, for semiconductor applications, it is preferable that the container has a high degree of cleanliness and less elution of impurities therefrom. Examples of usable containers include, but are not limited to, "CLEAN BOTTLE" series (manufactured by Aicello Chemical Co., Ltd.) and "PURE BOTTLE" (manufactured by Kodama Plastics Co., Ltd.).

The container or the inner wall of the accommodating portion thereof is preferably formed of a resin different from one or more resins selected from the group consisting of a polyethylene resin, a polypropylene resin, and a polyethylene-polypropylene resin, or a metal subjected to a rust prevention or metal elution prevention treatment. As the above-mentioned different resins, a fluorine-based resin (perfluororesin) can be particularly preferably used. In this manner, by using a container in which the container or the inner wall of the accommodating portion thereof is made of a fluorine-based resin, the occurrence of a problem associated with the elution of oligomers of ethylene or propylene can be suppressed as compared with the case of using a container in which the container or the inner wall of the accommodating portion thereof is made of a polyethylene resin, a polypropylene resin, or a polyethylene-polypropylene resin. A specific example of such a container in which the container or the inner wall of the accommodating portion thereof is made of a fluorine-based resin may be, for example, a FluoroPurePFA composite drum manufactured by Entegris, Inc. In addition, containers described in JP1991-502677A (JP-H03-502677A), page 4 and the like, WO2004/016526A, page 3 and the like, and WO99/46309A, pages 9 and 16, and the like can also be used.

As will be described later, the liquid of the present invention is capable of removing an oxide of a Group III-V element. If necessary, the liquid of the present invention is capable of suppressing or preventing the elution of a Group III-V element to which the liquid of the present invention is applied, from the film of the element.

<Removal Liquid for Removing Oxide of Group III-V Element>

The removal liquid for removing an oxide of a Group III-V element according to the present invention is capable of removing an oxide of a Group III-V element. If necessary, the removal liquid is capable of suppressing or preventing the elution of a Group III-V element to which the removal liquid is applied, from the film of the element.

<Oxidation Prevention Liquid for Preventing Oxidation of Group III-V Element>

The oxidation prevention liquid for preventing the oxidation of a Group III-V element according to the present invention is capable of suppressing or preventing the oxidation of a Group III-V element, especially a Group III-V element having a low degree of progress of oxidation and/or a Group III-V element after the removal of an oxide. If necessary, the oxidation prevention liquid is capable of suppressing or preventing the elution of a Group III-V element to which the oxidation prevention liquid is applied, from the film of the element.

<Treatment Liquid for Treating Compound of Group III-V Element>

The treatment liquid for treating a compound of a Group III-V element according to the present invention is capable of removing an oxide of a Group III-V element and is capable of suppressing or preventing the oxidation of a Group III-V element after the removal of an oxide. If necessary, the compound treatment liquid is capable of suppressing or preventing the elution of a Group III-V element to which the compound treatment liquid is applied, from the film of the element.

<Treatment Liquid for Treating Semiconductor Substrate>

The treatment liquid for treating a semiconductor substrate according to the present invention is applied to a semiconductor substrate (a compound of a Group III-V element present thereon) and is capable of removing an oxide of a Group III-V element and/or is capable of suppressing or preventing the oxidation of a Group III-V element. If necessary, the treatment liquid is capable of suppressing or preventing the elution of a Group III-V element from the film of the element. The treatment liquid for treating a semiconductor substrate according to the present invention may also be used as a rinsing liquid.

[Treatment Method (Method of Removing Oxide)]

With respect to the method of removing an oxide according to the present invention, the embodiment thereof is not particularly limited. For example, a batchwise treatment using a bath or a treatment using a single sheet type apparatus may be employed. Specifically, in the bath treatment, a semiconductor substrate or semiconductor substrate product having, for example, an oxide of a Group III-V element can be immersed and treated in a bath filled with the liquid of the present invention. It is preferred that the single sheet type apparatus has a treatment tank, and the above-mentioned semiconductor substrate is transferred or rotated in the treatment tank, and the above-mentioned stripping liquid is applied (by ejecting, spraying, flowing down, dropwise adding, or the like) into the treatment tank so that the stripping liquid is brought into contact with the semiconductor substrate.

The treatment temperature of the liquid of the present invention is preferably 10° C. or higher and more preferably 20° C. or higher. The upper limit is preferably 80° C. or lower, more preferably 60° C. or lower, and particularly preferably 40° C. or lower. The treatment temperature is based on the temperature applied to the substrate in the single sheet type apparatus. The treatment temperature may be set to the storage temperature or the temperature inside the tank in the case where it is managed by the batch treatment or the temperature in the circulation flow path in the case where it is managed by the circulation system.

In the above-mentioned removal method, as described above, a semiconductor substrate, a semiconductor substrate product, or the like is brought into contact with the liquid of the present invention to remove an oxide, and thereafter, it may or may not be washed (rinsed). In the case of being rinsed, for example, water, isopropanol or a mixed liquid thereof can be used as a rinsing liquid which can be used. Among them, most preferred is water. The temperature of the rinsing liquid is not particularly limited and can be set to an appropriate temperature which is preferably room temperature (25° C.).

The above-mentioned oxide of a Group III-V element (film) is preferably removed at a high removal rate. The removal rate [R2] as viewed from a film of an oxide of a Group III-V element is not particularly limited, but in consideration of production efficiency, it is preferably 10 Å/min or more, more preferably 50 Å/min or more, and particularly preferably 100 Å/min or more. The upper limit is not particularly limited, but it is practically 1,000 Å/min or less.

The exposed width of an oxide film of a Group III-V element is not particularly limited, but it is preferably 2 nm or more and more preferably 4 nm or more from the viewpoint that the advantages of the present invention become more remarkable. Similarly, from the viewpoint of remarkable effects, the upper limit value is practically 1,000 nm or less, preferably 100 nm or less, and more preferably 20 nm or less.

The elution rate (also referred to as a removal rate or metal elution rate) [R1] of the film of a Group III-V element is not particularly limited, but it is preferred that the element is not excessively removed. The elution rate is more preferably 100 Å/min or less, still more preferably 60 Å/min or less, and particularly preferably 40 Å/min or less. The lower limit is not particularly limited, but it is practically 0.1 Å/min or more in consideration of the measurement limit.

In the selective removal of an oxide film of a Group III-V element and a film of a Group III-V element, the removal rate ratio ([R2]/[R1]) is preferably 2 or more, more preferably 5 or more, and particularly preferably 10 or more. The upper limit is practically 300 or less and more practically 200 or less although it is not particularly specified and a higher value is preferable.

Further, with the liquid of the present invention according to a preferred embodiment of the present invention, since damage and elution of a metal electrode layer of Al, W, or the like, or an insulating film layer of HfO, HfSiO, WO, $AlO_x$, $SiO_2$, SiOC, SiON, SiOCN, TiN, SiN, TiAlC, or the like can also be suitably suppressed, the liquid of the present invention is also preferably applied to a semiconductor substrate containing them. In the present specification, in the case where a composition of a metal compound is expressed by a combination of its elements, it means an arbitrary composition is broadly included. For example, SiOC (SiON) means that Si, O and C (N) coexist, and does not mean that the ratio of the amounts is 1:1:1. This is common in the present specification, and the same applies to the other metal compounds.

An oxide of a Group III-V element is removed by the above-mentioned removal method. At this time, if necessary, the elution of a Group III-V element (metal) from the film of the element can be suppressed or prevented. Furthermore, the (re)oxidation of a Group III-V element can be suppressed or prevented.

[Treatment Method (Method of Preventing Oxidation of Group III-V Element)]

The method of preventing the oxidation of a Group III-V element is preferably applied to a Group III-V element (particularly a Group III-V element having a low degree of progress of oxidation) or a Group III-V element from which an oxide has been removed. This method is the same as the above-mentioned removal method except that the application target is not an oxide of a Group III-V element. Accordingly, the oxidation prevention liquid for preventing the oxidation of a Group III-V element is capable of suppressing or preventing the (re)oxidation of a Group III-V element. Although the reason for this is not clear in detail, it is thought to be due to the formation of a film (protective film) of a mercapto compound by interaction (for example, physical or chemical adsorption) between the Group III element of a Group III-V element, for example, As and the SH group of the mercapto compound.

[Treatment Method (Method of Treating Compound of Group III-V Element)]

The method of treating a compound of a Group III-V element is preferably applied to a compound of a Group III-V element. In the method of treating a compound of a Group III-V element, the application target is specified as an oxide of a Group III-V element and a Group III-V element, but the method is usually the same as the above-mentioned removal method. Since the treatment liquid for treating a compound of a Group III-V element according to the present invention has an action of removing an oxide and an action of preventing the oxidation of a compound, such a treatment liquid is capable of removing an oxide of a Group III-V element and is also capable of suppressing or preventing the (re)oxidation of a Group III-V element from which an oxide has been removed, even when the treatment liquid is of one-liquid type. The action of removing an oxide and the action of preventing the oxidation of a Group III-V element are as described above.

[Treatment Method (Method of Treating Semiconductor Substrate)]

The method of treating a semiconductor substrate of a Group III-V element is preferably applied to a compound of a Group III-V element present in the semiconductor substrate. This treatment method is usually the same as the above-mentioned removal method.

[Semiconductor Substrate Product]

FIG. 1 is a perspective view schematically showing a part of a structure of a FinFET to which the liquid of the present invention such as the above-mentioned removal liquid can be suitably applied. The feature of FinFET is that the conductive channel is covered with thin "fin" shaped silicon constituting the gate of the device. The term FinFET is a word coined by the University of California's Berkeley Laboratory. Based on the conventional DELTA design, it was applied to explain the construction of a nonplanar double-gate transistor on a SOI substrate. However, the word does not have a fixed definition. It is sometimes described as the architecture of a multi-gate transistor using certain fin. According to the multi-gate/tri-gate architecture with FinFET, the possibility of further process miniaturization increases. There is a possibility that the gate leakage current can be minimized and it is possible to be easily produced using a standard lithography technology.

Structurally, it has a three-dimensional structure laid out on a two-dimensional substrate. If the substrate area is the same, the gate volume becomes larger than that of a planar transistor. Since the gate has a structure of "wrapping" the channel, the channel's controllability of the gate is high and the leakage current when the device is in the off state is reduced. Therefore, it is possible to set a low threshold voltage and it is possible to obtain a preferable switching speed and power consumption.

In a preferred embodiment of the present invention, it is possible to suitably cope with the formation of the above-mentioned FinFET structure. In particular, it exhibits a suitable performance for the removal of an oxide film of a Group III-V element used for a source electrode, a drain electrode, or the like. Further, according to the requirements, it is possible to form a clean film surface by suppressing damage and elution of a Group III-V element from the surface of the film of the element. More preferably, the (re)oxidation of a Group III-V element (metal) can be suppressed to maintain a clean film surface after the removal of an oxide film of a Group III-V element.

Alternatively, in addition to the production of the above-mentioned FinFET, the liquid of the present invention can also be applied to the production of a GAA structure or a general MOSFET if necessary, and the effect thereof can be exerted. It should be noted that the gate-all-around (GAA) FET is a structure of a concept similar to that of FinFET except that the entire side of the channel portion is surrounded by a gate material. Depending on the design, the GAAFET will have two or three effective gates.

Figure 2:
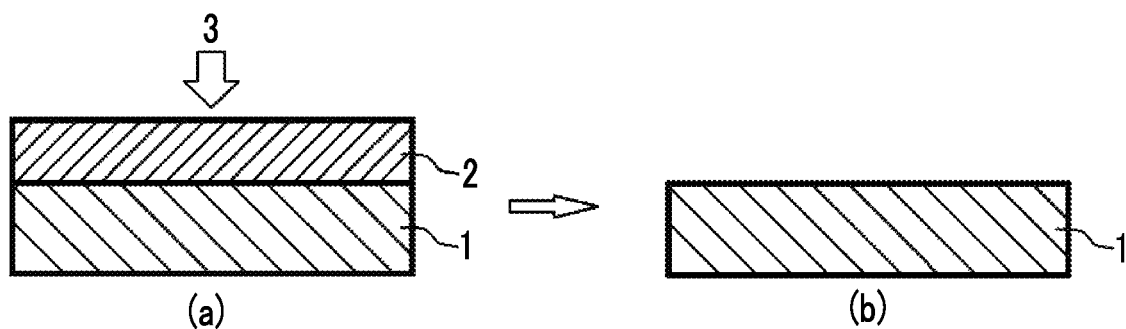
FIG. 2 is a cross-sectional view schematically showing an embodiment of the removal of an oxide film (oxide) of a Group III-V element.

FIG. 2(a) shows a state in which an oxide film 2 is formed on a film 1 of a Group III-V element. A liquid 3 of the present invention such as the above-mentioned removal liquid is applied thereto. As a result, only the oxide film 2 of a Group III-V element is suitably removed to result in the state of FIG. 2(b). On the other hand, since the liquid of the present invention does not exhibit excessive damage and elution for a Group III-V element, the film 1 of a Group III-V element is maintained in a clean state. Further, the liquid of the present invention is preferably capable of preventing the (re)oxidation of a Group III-V element and, also from this point, the film 1 of a Group III-V element is maintained in a clean state. As a result, a semiconductor substrate product with good quality can be delivered to the next step. Although the oxide is shown as an oxide film, here, for the convenience of illustration, the present invention is not limited thereto and can also be suitably applied to the removal of oxide residues such as particulate oxide and amorphous oxide.

Figure 3:
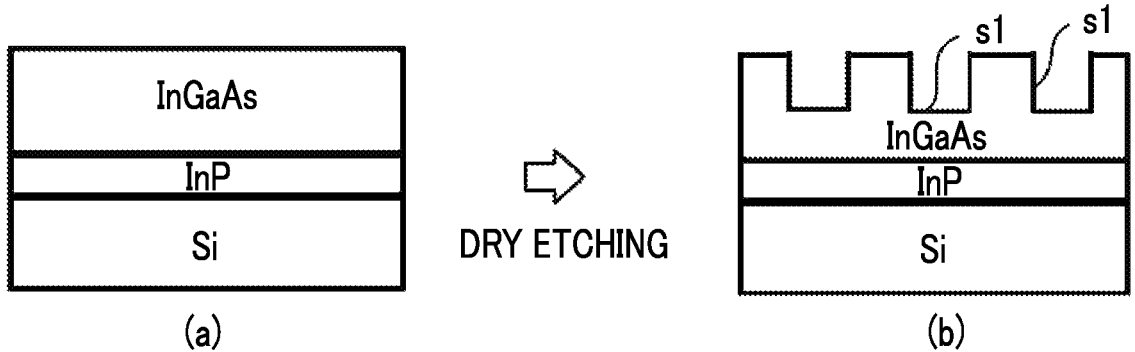
FIG. 3 is a cross-sectional view of a substrate showing a portion of a preparation process of a FinFET.

FIG. 3 is a cross-sectional view of a substrate showing a portion of a preparation process of a FinFET (hatching is omitted). In this step, a substrate in which InGaAs/InP/Si are stacked in that order is prepared (step (a)), and a predetermined pattern is formed on the uppermost layer InGaAs by dry etching (step (b)). The illustration of the resist film is omitted. After the dry etching described above, the residue of oxide film and oxide remains on the surface s1. In order to remove such a residue of oxide film and oxide, the liquid of the present invention such as the above-mentioned removal liquid can suitably exhibit its effect. In addition, the liquid of the present invention can suitably exhibit its effect of preventing the (re)oxidation of InGaAs from which the residue of oxide film and oxide has been removed in this manner.

Figure 4:
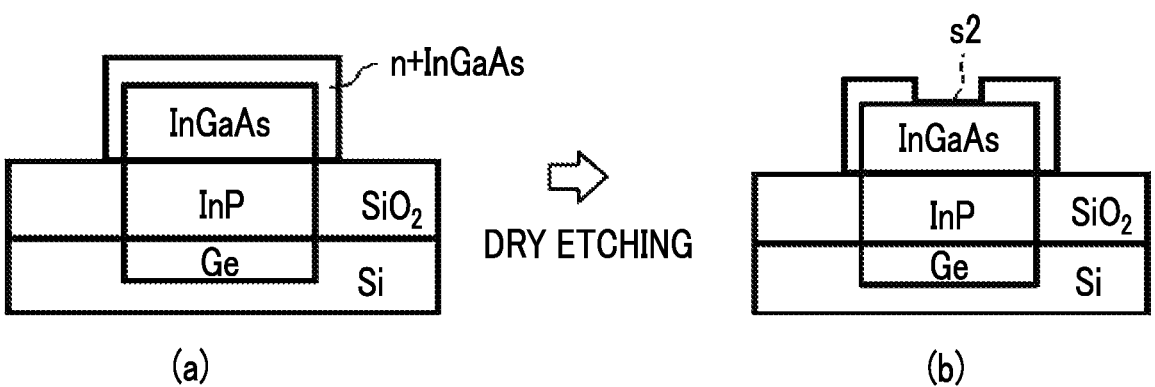
FIG. 4 is a cross-sectional view of a substrate showing another example of a preparation process of a FinFET.

FIG. 4 is a cross-sectional view of a substrate showing another example of a preparation process of a FinFET (hatching is omitted). Also in this step, the residue of oxide film and oxide of InGaAs remains on the surface s2. For such a situation, the liquid of the present invention such as the above-mentioned removal liquid can suitably exhibit its effect. In addition, the liquid of the present invention can suitably exhibit its effect of preventing the (re)oxidation of InGaAs from which the residue of oxide film and oxide has been removed in this manner.

In addition, the liquid of the present invention such as the above-mentioned removal liquid can exhibit its effect, for example, also in the treatment of post-CMP (pCMP). In the CMP step, for example, protrusions of InGaAs may be scraped off. An oxide film may be formed or an oxide residue may remain on the surface after being scraped off. For such a situation, the liquid of the present invention can suitably exhibit its effect. In addition, the liquid of the present invention can suitably exhibit its effect of preventing the (re)oxidation of InGaAs from which the residue of oxide film and oxide has been removed in this manner.

The treatment with the liquid of the present invention is preferably carried out under the conditions that light of 500 nm or less is blocked (for example, treated under yellow lamp or red lamp condition) or under dark room conditions. This is because a photo-illumination reaction proceeds when there is light irradiation, and the effect of removing oxides may be reduced.

In the semiconductor substrate to which the liquid of the present invention is applied as described above, the oxide of a Group III-V element is removed and more preferably the oxidation of a Group III-V element is also suppressed or prevented, whereby a clean surface is retained. Therefore, the time until the semiconductor substrate to which the liquid of the present invention has been applied is subjected to the next step is not particularly limited. For example, 4 hours or longer, preferably 10 hours or longer, and more preferably 24 hours or longer can be ensured.

In the present specification, the semiconductor substrate is used to mean not only a wafer but also an entire substrate structure provided with a circuit structure thereon. The semiconductor substrate member refers to a member constituting the semiconductor substrate as defined above and may be made of one material or a plurality of materials. It should be noted that the processed semiconductor substrate may be distinguished and referred to as a semiconductor substrate product in some cases, and if necessary, further distinguishably, a chip taken out by dicing following further processing and the processed product thereof are referred to as a semiconductor device. That is, in a broad sense, a semiconductor device and a semiconductor product incorporating the semiconductor device belong to the semiconductor substrate product.

In the present specification, application of a treatment liquid to a semiconductor substrate or a semiconductor substrate product is referred to as "application", but the embodiment thereof is not particularly limited. For example, it broadly includes bringing the liquid of the present invention into contact with the substrate, specifically, in which this bringing into contact may be carried out by means of an immersion in a batchwise manner or by means of ejection in a single sheet manner.

In the above-mentioned semiconductor substrate product, the case of using the liquid of the present invention has been described. However, in the present invention, similarly to the case of using the liquid of the present invention, the cases of using the removal liquid for removing an oxide of a Group III-V element according to the present invention, the oxidation prevention liquid for preventing the oxidation of a Group III-V element according to the present invention, the treatment liquid for treating a compound of a Group III-V element according to the present invention, and the treatment liquid for treating a semiconductor substrate can also be suitably applied to the semiconductor substrate shown in each of the above-mentioned figures and the same action and effect can be obtained.

The liquid of the present invention used in various methods of the present invention can be reused. Although not particularly limited, it is preferable that the used liquid is recovered or circulated for reuse instead of being discarded after one use (without reuse), and the used liquid is reused in the above-mentioned various methods, for example, the removal method, the oxidation prevention method, the treatment method and/or the treatment method of a semiconductor substrate. It may also be used as a rinsing liquid.

In the case where the liquid of the present invention is circulated and reused, it can be used for 1 hour or longer and can be repeatedly used. The upper limit of the circulation time is not particularly limited, but since the treatment performance is deteriorated, it is preferable to be exchanged within 1 week, more preferably within 3 days, and particularly preferably to be replaced with a new liquid every single day. In addition, the circulation of the liquid is preferably carried out in a hermetically sealed system as much as possible, or under a nitrogen flow. A nitrogen flow is more preferred.

In the case where the circulation of the liquid is carried out in a line form, the set temperature of the liquid may be determined according to the line configuration or the treatment performance as appropriate, but it is typically favorable to set and manage the temperature of the tank storing the liquid. The set temperature of the liquid may be managed according to the surface temperature of the object to which the liquid of the present invention is applied, as long as the measurement and management are possible, such as in the case where more severe conditions are required in terms of performance.

EXAMPLES

Hereinafter, the present invention will be described in more detail with reference to the following Examples, but the present invention is not limited thereto. The % and parts given as formulations and blending amounts in the Examples are on a mass basis unless otherwise specified.

Example 1 and Comparative Example 1

(Preparation of Test Substrate)
A Si film was epitaxially grown on a commercially available silicon substrate. Furthermore, a film of InGaAs or InP was formed on the Si epitaxial layer. This was treated to form an oxide film of InGaAs or InP on a part of the substrate to prepare a test substrate.

(Removal Test of Oxide Film)
Each removal liquid (also referred to as a chemical liquid) having the composition shown in Table 1 was prepared and a beaker test was carried out using the above test substrate. Specifically, while stirring the chemical liquid at room temperature (25° C.) at 250 rpm, a part of the test substrate was cut into a beaker and treated with each removal liquid for 2 minutes. The above treatment was carried out under a yellow lamp (yellow light). The pH of the chemical liquid of Test No. 101 was 0.1. The substrate after the chemical liquid treatment was stored for 4 hours under ambient atmosphere and under yellow light.

(Performance Evaluation)
<Oxide Film Removing Ability and Reoxidation Inhibiting Ability>
For the oxide film removing ability, the substrate surface after treatment was measured by X-ray photoelectron spectroscopy (ESCA) and analyzed for each component constituting each substrate. Specifically, In, Ga, and As were analyzed in the case of InGaAs. Evaluation of peelability (oxide film removing ability) was carried out on the basis of an element with the least removing ability of an oxide film by any one of the measured elements. Specifically, the ratio [P2/P1] of the peak (P2) of the oxide to the peak (P1) of the non-oxide was taken as the oxide film peeling performance and reoxidation preventing performance, and evaluation was carried out by the following category. The results are shown in Table 1.

AA: [P2/P1]<0.02
A: 0.02≤[P2/P1]<0.04
B: 0.04≤[P2/P1]<0.05
C: 0.05≤[P2/P1]<0.06
D: 0.06≤[P2/P1]

<Metal Elution Property>
For the elution of metals (In, Ga, As and P elements), the metal film (InGaAs film and InP film) from which an oxide film had been removed was immersed in the corresponding chemical liquid and evaluated before and after the treatment. Specifically, the film thickness was measured by ellipsometry and evaluated based on the following standards. Specifically, the thickness T of the removed film was calculated by measuring the film thicknesses before and after the treatment using ellipsometry (using VASE spectroscopic ellipsometer, manufactured by J. A. Woollam Japan Corp.). The average value $T^{AV}$ at 5 points was adopted (measurement conditions were as follows: measurement range: 1.2 to 2.5 eV and measurement angle: 70 degrees and 75 degrees). The results are shown in Table 1.

AA: $T^{AV}$<1 Å/process time (immersion time)
A: 1 Å/process time≤$T^{AV}$<3 Å/process time
B: 3 Å/process time≤$T^{AV}$<6 Å/process time
C: 6 Å/process time≤$T^{AV}$ <Stability>
The liquid prepared in Test No. 103 was stored in an environment of 40° C. for 2 months, and the performance evaluation of the foregoing sections <Oxide film removing ability and reoxidation inhibiting ability> and <Metal elution property> was carried out. As a result, the same results as those shown in "Test No. 103" in Table 1 below were obtained, and it was found that the initial function was retained even by storage over time, and the stability was excellent.

<Recyclability>
Ten sheets of test substrates (1 cm×2 cm square coupons) were sequentially (successively) immersed in 200 mL of the liquid prepared in Test No. 103 in the same manner as in the foregoing section (Removal test of oxide film), and the removal test of an oxide film was carried out to evaluate the foregoing <Oxide film removing ability and reoxidation inhibiting ability> and <Metal elution property>. As a result, the same results as those shown in "Test No. 103" in Table 1 below were obtained in any test substrate. Accordingly, it was found that the liquid prepared in Test No. 103 was equivalent in performance to the first test substrate and the tenth test substrate and exhibited excellent recyclability.

TABLE 1

| Test No. | Acid | Content (%) | Mercapto compound | Content (%) | Organic solvent | Content (%) | Water Content (%) | Oxide film removing ability and reoxidation inhibiting ability | | Metal elution | | Remarks |
|---|---|---|---|---|---|---|---|---|---|---|---|---|
| | | | | | | | | InGaAsOx | InPOx | InGaAs | InP | |
| 101 | 36% HCl | 10 | thiomalic acid | 0.1 | — | | 89.9 | B | A | AA | A | Present invention |

TABLE 1-continued

| Test No. | Acid | Content (%) | Mercapto compound | Content (%) | Organic solvent | Content (%) | Water Content (%) | Oxide film removing ability and reoxidation inhibiting ability InGaAsOx | InPOx | Metal elution InGaAs | InP | Remarks |
|---|---|---|---|---|---|---|---|---|---|---|---|---|
| 102 | 36% HCl | 10 | thiomalic acid | 0.5 | | | 89.5 | A | A | AA | A | Present invention |
| 103 | 36% HCl | 10 | thiomalic acid | 1.0 | | | 89.0 | A | A | AA | A | Present invention |
| 104 | 36% HCl | 10 | thiomalic acid | 3.0 | | | 87.0 | A | A | AA | A | Present invention |
| 105 | 36% HCl | 10 | thiomalic acid | 1.0 | DMSO | 89 | 0.0 | A | A | B | AA | Present invention |
| 106 | 36% HCl | 10 | α-thioglycerol | 0.7 | | | 89.3 | B | A | A | AA | Present invention |
| 107 | 36% HCl | 10 | 2-mercaptopyridine | 0.1 | | | 89.9 | A | A | A | A | Present invention |
| 108 | 36% HCl | 10 | 2-mercaptopyridine | 0.2 | | | 89.8 | AA | A | A | A | Present invention |
| 109 | 36% HCl | 10 | 2-mercaptopyridine | 0.5 | | | 89.5 | AA | A | A | A | Present invention |
| 110 | 36% HCl | 5 | 2-mercaptopyridine | 0.2 | | | 94.8 | AA | A | A | A | Present invention |
| 111 | 36% HCl | 15 | 2-mercaptopyridine | 0.2 | | | 84.8 | AA | A | A | A | Present invention |
| 112 | 36% HCl | 10 | thioglycolic acid | 1.2 | | | 88.8 | B | A | A | A | Present invention |
| 113 | 36% HCl | 10 | thioglycolic acid | 2.4 | | | 87.6 | AA | A | A | A | Present invention |
| 114 | 36% HCl | 10 | L-cysteine | 0.8 | | | 89.2 | A | A | AA | A | Present invention |
| 115 | 36% HCl | 10 | L-cysteine | 2.4 | | | 87.6 | AA | A | AA | A | Present invention |
| 116 | 36% HCl | 10 | 2-mercaptopyrimidine | 0.2 | | | 89.8 | B | A | A | A | Present invention |
| 117 | 36% HCl | 10 | 1H-1,2,4-triazole-3-thiol | 0.2 | | | 89.8 | B | A | A | A | Present invention |
| 118 | 49% HBr | 11 | thiomalic acid | 1.0 | | | 88.0 | A | A | AA | A | Present invention |
| 119 | 49% HBr | 11 | 2-mercaptopyridine | 0.2 | | | 88.8 | AA | A | A | A | Present invention |
| 120 | 49% HBr | 11 | L-cysteine | 2.4 | | | 86.6 | AA | A | A | A | Present invention |
| c01 | 36% HCl | 10 | — | — | | | 90.0 | C | A | A | B | Comparative Example |
| c02 | 36% HCl | 20 | — | — | | | 80.0 | C | A | B | C | Comparative Example |
| c03 | 36% HCl | 10 | QUARTAMIN 60W | 0.17 | | | 89.8 | C | A | B | B | Comparative Example |
| c04 | 36% HCl | 10 | TBAC | 1.00 | | | 89.0 | C | A | B | B | Comparative Example |
| c05 | 36% HCl | 10 | oxalic acid | 0.84 | | | 89.2 | C | A | B | C | Comparative Example |
| c06 | 36% HCl | 10 | citric acid | 1.28 | | | 88.7 | C | A | B | B | Comparative Example |
| c07 | 47% HF | 30 | — | — | | | 70.0 | C | B | A | A | Comparative Example |
| c08 | 49% HBr | 20 | — | — | | | 80.0 | C | B | A | A | Comparative Example |
| c09 | 36% HCl | 10 | benzotriazole | 0.2 | | | 89.8 | C | A | A | A | Comparative Example |
| c10 | 36% HCl | 10 | 1-hydroxybenzotriazole | 0.2 | | | 89.8 | C | A | A | A | Comparative Example |
| c11 | 36% HCl | 10 | benzothiazole | 0.2 | | | 89.8 | C | A | A | A | Comparative Example |
| c12 | 36% HCl | 10 | thiazole | 0.2 | | | 89.8 | C | A | A | A | Comparative Example |
| c13 | 36% HCl | 10 | malic acid | 0.9 | | | 89.1 | C | A | A | A | Comparative Example |
| c14 | 36% HCl | 10 | glycolic acid | 0.6 | | | 89.4 | C | A | A | A | Comparative Example |
| c15 | 36% HCl | 10 | boric acid | 0.4 | | | 89.6 | C | A | A | A | Comparative Example |
| c16 | 36% HCl | 10 | methylboronic acid | 0.4 | | | 89.6 | C | A | A | A | Comparative Example |

<Annotation of Table>
InGaAsOx: oxide of InGaAs
InPOx: oxide of InP
TBAC: tetrabutylammonium chloride manufactured by TCI
HCl: hydrochloric acid aqueous solution in an amount of indicated mass % (manufactured by Wako)
HF: hydrofluoric acid aqueous solution in an amount of indicated mass %
HBr: hydrobromic acid aqueous solution in an amount of indicated mass %
Thiomalic acid: manufactured by Tokyo Chemical Industry Co., Ltd. (TCI)
α-thioglycerol: manufactured by Kanto Kagaku Co., Ltd.
2-mercaptopyridine: manufactured by Wako Pure Chemical Industries, Ltd.
Thioglycolic acid: manufactured by Wako Pure Chemical Industries, Ltd.
L-cysteine: manufactured by Wako Pure Chemical Industries, Ltd.
2-mercaptopyrimidine: manufactured by Wako Pure Chemical Industries, Ltd.
1H-1,2,4-triazole-3-thiol: manufactured by Wako Pure Chemical Industries, Ltd.
QUARTAMIN 60 W (trade name): manufactured by Kao Corporation (Cetyltrimethylammonium chloride)
Oxalic acid: manufactured by Wako Pure Chemical Industries, Ltd.
Citric acid: manufactured by Wako Pure Chemical Industries, Ltd.
Benzotriazole: manufactured by Wako Pure Chemical Industries, Ltd.
1-Hydroxybenzotriazole: manufactured by Wako Pure Chemical Industries, Ltd.
Benzothiazole: manufactured by Wako Pure Chemical Industries, Ltd.
Thiazole: manufactured by Wako Pure Chemical Industries, Ltd.
Malic acid: manufactured by Wako Pure Chemical Industries, Ltd.
Glycolic acid: manufactured by Wako Pure Chemical Industries, Ltd.
Boric acid: manufactured by Wako Pure Chemical Industries, Ltd.
Methylboronic acid: manufactured by Wako Pure Chemical Industries, Ltd.
DMSO: dimethylsulfoxide As can be seen from the results of Table 1 above, according to the removal liquid of the present invention, it was found that the removability of an oxide of a Group III-V element (oxide film removing ability) is high and on the other hand the elution of a Group III-V element (metal) from the film of the element can be suppressed. In addition, according to the removal liquid of the present invention, it was further found that the removal liquid of the present invention has a high reoxidation inhibiting ability of a Group III-V element.

In particular, it was further found that the removal liquid of the present invention is excellent in oxide film removing ability for InGaAs and reoxidation inhibiting ability for InGaAs (compound semiconductor) in which the conventional removal liquid such as an inorganic acid aqueous solution did not show sufficient oxide film removing ability and reoxidation inhibiting ability.

Example 2 and Comparative Example 2

Each removal liquid having the composition shown in Table 2 was prepared and the removal test of an oxide film was carried out using the test substrate (substrate on which an oxide film of InGaAs was formed) prepared in Example 1. Specifically, each substrate was subjected to a removal test of an oxide film in the same manner as in Example 1, except that the oxide film removing ability and the reoxidation inhibiting ability for each substrate were evaluated after storing the substrate after the chemical liquid treatment in the removal test of an oxide film for 4 hours and 24 hours in the ambient atmosphere under yellow light. The results are shown in Table 2.

In the column of "Oxide film removing ability and reoxidation inhibiting ability" of Table 2, the results of oxide film removing ability and reoxidation inhibiting ability after storage for 4 hours (Example 1 and Comparative Example 1) and the results of oxide film removing ability and reoxidation inhibiting ability after storage for 24 hours (Example 2 and Comparative Example 2) are shown.

Test No. and table annotations in Table 2 are the same as those in Table 1.

TABLE 2

| Test No. | Acid | Content (%) | Mercapto compound | Content (%) | Water Content (%) | Oxide film removing ability and reoxidation inhibiting ability for InGaAs | | Remarks |
|---|---|---|---|---|---|---|---|---|
| | | | | | | 4 hours | 24 hours | |
| 103 | 36% HCl | 10 | thiomalic acid | 1.0 | 89.0 | A | B | Present invention |
| 108 | 36% HCl | 10 | 2-mercaptopyridine | 0.2 | 89.8 | AA | AA | Present invention |
| 114 | 36% HCl | 10 | L-cysteine | 0.8 | 89.2 | A | B | Present invention |
| 115 | 36% HCl | 10 | L-cysteine | 2.4 | 87.6 | AA | AA | Present invention |
| 116 | 36% HCl | 10 | 2-mercaptopyrimidine | 0.2 | 89.8 | B | C | Present invention |
| 121 | 36% HCl | 10 | 1H-1,2,4-triazole-3-thiol | 0.4 | 89.6 | B | B | Present invention |
| 122 | 36% HCl | 10 | 2-mercaptopyridine and L-cysteine | 0.2 for each | 89.6 | AA | AA | Present invention |

TABLE 2-continued

| Test No. | Acid | Content (%) | Mercapto compound | Content (%) | Water Content (%) | Oxide film removing ability and reoxidation inhibiting ability for InGaAs 4 hours | Oxide film removing ability and reoxidation inhibiting ability for InGaAs 24 hours | Remarks |
|---|---|---|---|---|---|---|---|---|
| 123 | 36% HCl | 10 | 2-mercaptopyridine and citric acid | 0.2 for each | 89.6 | AA | AA | Present invention |
| 124 | 47% HF and 36% HCl | 5 for each | 2-mercaptopyridine | 0.2 | 89.8 | AA | AA | Present invention |
| c01 | 36% HCl | 10 | — | — | 90.0 | C | D | Comparative Example |
| c13 | 36% HCl | 10 | malic acid | 0.9 | 89.1 | C | D | Comparative Example |

As can be seen from the results of Table 2 above, according to the removal liquid of the present invention, it was found that it is possible to more effectively suppress the reoxidation of a Group III-V element, in addition to having the removability of an oxide of a Group III-V element.

Example 3 and Comparative Example 3

Each removal liquid having the composition shown in Table 3 was prepared. Using the test substrate (substrate on which an oxide film of InGaAs was formed) prepared in Example 1, the removal test of an oxide film was carried out in the same manner as in Example 1 to measure an oxide film removal rate [R2], a metal elution rate [R1], and a removal rate ratio ([R2]/[R1]).

The metal elution rate [R1] was determined by converting the elution amount of InGaAs (each element of In, Ga, and As) into a film thickness and dividing the converted value by the process time.

The oxide film removal rate [R2] was determined by converting the removal amount of the InGaAs oxide into a film thickness and dividing the converted value by the process time.

In each removal liquid, the ratio of the content [content of acid/content of mercapto compound] was calculated and is shown in Table 3.

Test No. and table annotations in Table 3 are the same as those in Table 1.

<Oxide Film Removal Rate [R2]>

The oxide film removal rate [R2] determined as described above was evaluated by the following evaluation category (unit: Å/min). The results are shown in Table 3.

A: 10≤[R2]
B: 3≤[R2]<10
C: 1≤[R2]<3
D: [R2]<1

<Metal Elution Rate [R1]>

The metal elution rate [R1] determined as described above was evaluated by the following evaluation category (unit: A/min). The results are shown in Table 3.

AA: [R1]<2
A: 2≤[R1]<5
B: 5≤[R1]<10
C: 10≤[R1]

<Removal Rate Ratio>

The removal rate ratio ([R2]/[R1]) was calculated from the metal elution rate [R1] and the oxide film removal rate [R2] determined as described above and then evaluated by the following evaluation category. The results are shown in Table 3.

A: 10≤[R2]/[R1]
B: 2≤[R2]/[R1]<10
C: [R2]/[R1]<2

TABLE 3

| Test No. | Acid | Content (%) | Mercapto compound | Content (%) | Content ratio (solids) [content of mercapto compound/ content of acid] | Organic solvent | Content (%) | Water Content (%) | [R2] oxide film removal rate InGaAsOx | [R1] metal elution rate InGaAs | Removal rate ratio [R2]/[R1] | Remarks |
|---|---|---|---|---|---|---|---|---|---|---|---|---|
| 101 | 36% HCl | 10 | thiomalic acid | 0.1 | 36 | — | | 89.9 | A | AA | A | Present invention |
| 125 | 36% HCl | 10 | thiomalic acid | 0.5 | 7.2 | propylene glycol | 15 | 74.5 | A | AA | A | Present invention |
| 126 | 36% HCl | 10 | thiomalic acid | 1.0 | 3.6 | N-methyl-2-pyrrolidone | 15 | 74.0 | A | AA | A | Present invention |
| 127 | 36% HCl | 10 | thiomalic acid | 3.0 | 1.2 | propylene glycol and diethylene glycol monoethyl ether | 7.5 for each | 87.0 | A | AA | A | Present invention |
| 128 | 36% HCl | 1 | thiomalic acid | 1.0 | 0.36 | — | | 98.0 | B | AA | B | Present invention |
| 129 | 36% HCl | 20 | thiomalic acid | 3.0 | 2.4 | — | | 77.0 | A | AA | A | Present invention |

TABLE 3-continued

| Test No. | Acid | Content (%) | Mercapto compound | Content (%) | Content ratio (solids) [content of mercapto compound/ content of acid] | Organic solvent | Content (%) | Water Content (%) | [R2] oxide film removal rate InGaAsOx | [R1] metal elution rate InGaAs | Removal rate ratio [R2]/[R1] | Remarks |
|---|---|---|---|---|---|---|---|---|---|---|---|---|
| 130 | 36% HCl | 0.1 | thiomalic acid | 1.0 | 0.036 | — | | 80.0 | C | AA | B | Present invention |
| 131 | 36% HCl | 0.1 | thiomalic acid | 3.0 | 0.01 | — | | 80.0 | C | AA | B | Present invention |
| 132 | 36% HCl | 1 | thiomalic acid | 0.5 | 0.72 | — | | 98.5 | B | AA | B | Present invention |
| 133 | 36% HCl | 25 | thiomalic acid | 0.09 | 100 | — | | 74.9 | A | AA | A | Present invention |
| 134 | 36% HCl | 25 | thiomalic acid | 0.06 | 150 | — | | 74.9 | A | A | A | Present invention |
| c126 | 36% HCl | 0 | thiomalic acid | 1.0 | 0 | — | | 90.0 | D | — | C | Comparative Example |

As can be seen from the results in Table 3, according to the removal liquid of the present invention, it was found that an oxide of a Group III-V element can be removed at a high removal rate [R2], and furthermore, the elution of a Group III-V element (Group III-V semiconductor) can be suppressed effectively. Thus, it was found that the removal liquid of the present invention is capable of removing an oxide film of a Group III-V element with high selectivity.

From the results of Examples 1 to 3, the following can be seen.

In the above-mentioned Examples 1 to 3, the removal liquid of the present invention was used. But even in the case where the treatment liquid for treating a compound of a Group III-V element or the oxidation prevention liquid for preventing the oxidation of a Group III-V element according to the present invention, each having the same composition as each of the above-mentioned removal liquids, was used in place of such a removal liquid, the same excellent effects as those described above can be obtained. Further, even in the case where a semiconductor substrate having a compound of a Group III-V element in place of the above-mentioned test substrate was treated by the treatment liquid for treating a semiconductor substrate according to the present invention having the same composition as each of the above-mentioned removal liquids, the same excellent effects as those described above can be obtained. Thus, it is possible to produce a desired semiconductor substrate product.

While the present invention has been described in conjunction with the embodiments thereof, it is not intended to limit the present invention to any detail in the description, unless otherwise indicated, and it should be interpreted broadly without departing from the spirit and scope of the present invention as set forth in the appended claims.

This application claims priority based on JP2015-25478 filed on Feb. 12, 2015, and JP2016-18056 filed on Feb. 2, 2016, the disclosures of which are incorporated herein by reference in their entireties.

EXPLANATION OF REFERENCES

1: film of Group III-V element
2: oxide film of Group III-V element
3: removal liquid

What is claimed is:

1. A removal liquid for removing an oxide of a Group III-V element, comprising:

hydrochloric acid or hydrofluoric acid; and
a mercapto compound represented by the following Formula (1) or (4)

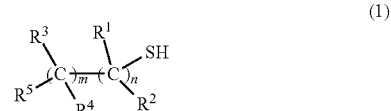

(1)

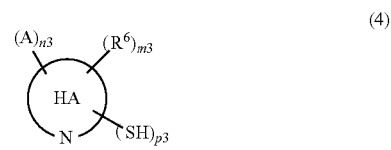

(4)

where $R^1$ to $R^5$ are each independently a hydrogen atom, a thiol group, a hydroxyl group, a carboxyl group, an alkyl group, an alkenyl group, an aryl group, an aralkyl group, an amino group, an acyl group, or an acylamino group, and $R^1$ to $R^5$ may be bonded to one another to form a ring;

m and n are an integer and m+n is an integer of 1 to 12;
one or more of $R^1$ to $R^5$ in a molecule are present as a carboxyl group;
A is a carboxyl group or a hydroxyl group;
$R^6$ is an alkyl group, an alkenyl group, an aryl group, an aralkyl group, an amino group, an acyl group, or an acylamino group;
HA represents a structure obtained by removing m3+n3+p3 number of hydrogen atoms from a pyridine ring; and
n3 is an integer of 1 to 4 and m3 is an integer of 0 to 5, and p3 is an integer of 1 to 4,
wherein the content of the acid if 0.05 mass% or more and 20 mass% or less,
the content of the mercapto compound is 0.01 mass% or more and 10 mass% or less, and
a content ratio in terms of mass ratio between the content of the mercapto compound and the content of the acid is from 0.3 to 500.

2. The removal liquid according to claim 1, wherein the mercapto compound contains at least one of a carboxyl group or a hydroxyl group, and a thiol group.

3. The removal liquid according to claim 1, wherein the mercapto compound has 1 to 12 carbon atoms and one or more and four or less thiol groups within a molecule.

4. The removal liquid according to claim 1, which comprises hydrochloric acid.

5. The removal liquid according to claim 1, wherein the elution of a Group III-V element is suppressed or prevented and an oxide of a Group III-V element is removed.

6. The removal liquid according to claim 1, wherein the Group III-V element is at least one selected from In, Ga, As, and P.

7. The removal liquid according to claim 4, wherein the concentration of hydrochloric acid in the liquid is 0.1 mass% or more 10 mass% or less.

8. The removal liquid according to claim 1, wherein the content ratio of the content of the mercapto compound/the content of hydrochloric acid or hydrofluoric acid is 0.3 to 150.

9. The removal liquid according to claim 4, wherein the content ratio of the content of the mercapto compound/the content of hydrochloric acid is 0.3 to 150.

10. A treatment liquid for treating a semiconductor substrate, comprising:
an acid; and
a mercapto compound having 3 to 12 carbon atoms,
wherein the mercapto compound contains a thiol group and at least one of a carboxyl group,
the content of the acid is 0.05 mass% or more and 20 mass% or less,
the content of the mercapto compound is 0.01 mass% or more and 10 mass% or less, and
a content ratio in terms of mass ratio between the content of the mercapto compound and the content of the acid is from 0.3 to 500.

11. The treatment liquid according to claim 10, wherein the acid is hydrochloric acid.

12. The treatment liquid according to claim 11, wherein the concentration of hydrochloric acid in the liquid is 0.1 mass% or more and 10 mass% or less.

13. The treatment liquid according to claim 10, wherein the content ratio of the content of the mercapto compound/the content of the acid is 0.3 to 150.

14. The treatment liquid according to claim 11, wherein the content ratio of the content of the mercapto compound/the content of hydrochloric acid is 0.3 to 150.

15. A removal method for removing an oxide of a Group III-V element, comprising:
applying a treatment liquid containing an acid and a mercapto compound to an oxide of a Group III-V element to remove the oxide of a Group III-V element,
wherein the mercapto compound is represented by the following Formula (1) or (4)

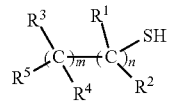

(1)

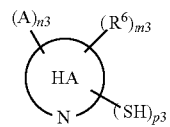

(4)

where $R^1$ to $R^5$ are each independently a hydrogen atom, a thiol group, a hydroxyl group, a carboxyl group, an alkyl group, an alkenyl group, an aryl group, an aralkyl group, an amino group, an acyl group, or an acylamino group, and $R^1$ to $R^5$ may be bonded to one another to form a ring;
m and n are an integer and m+n is an integer of 1 to 12;
one or more of $R^1$ to $R^5$ in a molecule are present as a carboxyl group or a hydroxyl group;
A is a carboxyl group or a hydroxyl group;
$R^6$ is an alkyl group, an alkenyl group, an aryl group, an aralkyl group, an amino group, an acyl group, or an acylamino group;
HA represents a structure obtained by removing m3+n3+p3 number of hydrogen atoms from a pyridine ring; and
n3 is an integer of 1 to 4 and m3 is an integer of 0 to 5, and p3 is an integer of 1 to 4,
wherein the treatment is carried out under a condition that light of 500 nm or less is blocked.

16. The removal method according to claim 15, wherein the elution of a Group III-V element is suppressed or prevented and an oxide of a Group III-V element is removed.

17. The removal method according to claim 15, wherein one or more of $R^1$ to $R^5$ in a molecule are present as a carboxyl group.

18. A method for producing a semiconductor substrate product free of an oxide film of a Group III-V element, which comprises providing a semiconductor substrate product having thereon a film of a Group III-V element, and an oxide film of a Group III-V element formed on the film of the Group III-V element, and removing the oxide film of a Group III-V element from the semiconductor substrate product by the removal method according to claim 15.

19. A treatment liquid for treating a compound of a Group III-V element, comprising:
hydrochloric acid or hydrofluoric acid; and
a mercapto compound,
wherein the mercapto compound contains a thiol group and at least one carboxyl group,
the content of the acid is 0.05 mass% or more and 20 mass% or less,
the content of the mercapto compound is 0.01 mass% or more and 10 mass% or less, and
a content ratio in terms of mass ratio between the content of the mercapto compound and the content of the acid is from 0.3 to 500.

20. The treatment liquid according to claim 19, which comprises hydrochloric acid.

21. The treatment liquid according to claim 20, wherein the concentration of hydrochloric acid in the liquid is 0.1 mass% or more and 10 mass% or less.

22. The treatment liquid according to claim 19, wherein the content ratio of the content of the mercapto compound/the content of hydrochloric acid or hydrofluoric acid 0.3 to 150.

23. The treatment liquid according to claim 20, wherein the content ratio of the content of the mercapto compound/the content of hydrochloric acid is 0.3 to 150.

24. An oxidation prevention liquid for preventing the oxidation of a Group III-V element, comprising:
hydrochloric acid or hydrofluoric acid; and
a mercapto compound,
wherein the mercapto compound contains a thiol group and at least one carboxyl group,
the content of the acid is 0.05 mass% or more and 20 mass% or less,
the content of the mercapto compound is 0.01 mass% or more and 10 mass% or less, and a content ratio in terms of mass ratio between the content of the mercapto compound and the content of the acid is from 0.3 to 500.

25. The oxidation prevention liquid according to claim 24, which comprises hydrochloric acid.

26. The oxidation prevention liquid according to claim 25, wherein the concentration of hydrochloric acid in the liquid is 0.1 mass% or more and 10 mass% or less.

27. The oxidation prevention liquid according to claim 24, wherein the content ratio of the content of the mercapto compound/the content of hydrochloric acid or hydrofluoric acid is 0.3 to 150.

28. The oxidation prevention liquid according to claim 25, wherein the content ratio of the content of the mercapto compound/the content of hydrochloric acid is 0.3 to 150.

29. A treatment liquid for treating a semiconductor substrate comprising a Group III-V element, containing an acid and a mercapto compound having 3 to 12 carbon atoms,
wherein the mercapto compound contains a thiol group and at least one carboxyl group,
the content of the acid is 0.05 mass% or more and 20 mass% or less,
the content of the mercapto compound is 0.01 mass% or more and 10 mass% or less, and
a content ratio in terms of mass ratio between the content of the mercapto compound and the content of the acid is from 0.3 to 500.

30. The treatment liquid according to claim 29, wherein the acid is an inorganic acid.

31. The treatment liquid according to claim 30, wherein the inorganic acid is hydrochloric acid.

32. The treatment liquid according to claim 29, wherein the elution of the Group III-V element is suppressed or prevented and an oxide of a Group III-V element is removed.

33. The treatment liquid according to claim 29, wherein the Group III-V element is at least one selected from In, Ga, As, and P.

34. The treatment liquid according to claim 29, wherein the mercapto compound is represented by any one of the following Formulae (1) to (4):

where $R^1$ to $R^5$ are each independently a hydrogen atom, a thiol group, a hydroxyl group, a carboxyl group, an alkyl group, an alkenyl group, an aryl group, an aralkyl group, an amino group, an acyl group, or an acylamino group, and $R^1$ to $R^5$ may be bonded to one another to form a ring;
m and n are an integer and m+n is an integer of 1 to 12;
one or more of $R^1$ to $R^5$ in a molecule are present as a carboxyl group;
A is a carboxyl group or a hydroxyl group;
Cy is a structure obtained by removing m1+n1+p1 number of hydrogen atoms from a cyclic aliphatic hydrocarbon;
$R^6$ is an alkyl group, an alkenyl group, an aryl group, an aralkyl group, an amino group, an acyl group, or an acylamino group;
n1, n2, p1, and p2 are an integer of 1 to 4 and m1 and m2 are an integer of 0 to 4, provided that n2+m2+p2 is 6 or less;
HA represents a structure obtained by removing m3+n3+p3 number of hydrogen atoms from an N-containing heteroaromatic ring; and
n3 is an integer of 1 to 4 and m3 is an integer of 0 to 5, and p3 is an integer of 1 to 4.

35. The treatment liquid according to claim 29, wherein the content ratio of the content of the mercapto compound/the content of the acid is 0.3 to 150.

36. The treatment liquid according to claim 31, wherein the concentration of hydrochloric acid in the liquid is 0.1 mass% or more and 10 mass% or less.

37. The treatment liquid according to claim 31, wherein the content ratio of the content of the mercapto compound/the content of hydrochloric acid is 0.3 to 150.

38. A treatment liquid for treating a semiconductor substrate comprising a Group III-V element, containing an acid and a mercapto compound having 1 to 12 carbon atoms,
wherein the mercapto compound contains one or more and four or less thiol groups within a molecule and at least one carboxyl group,
the content of the acid is 0.05 mass% or more and 20 mass% or less,
the content of the mercapto compound is 0.01 mass% or more and 10 mass% or less, and
a content ratio in terms of mass ratio between the content of the mercapto compound and the content of the acid is from 0.3 to 500.

39. A removal method for removing an oxide of InGaAs or InP, comprising:
applying a treatment liquid containing an acid and a mercapto compound to InGaAs or InP to remove the oxide InGaAs or InP,
wherein the mercapto compound is represented by the following Formula (1) or (4)

where $R^1$ to $R^5$ are each independently a hydrogen atom, a thiol group, a hydroxyl group, a carboxyl group, an alkyl group, an alkenyl group, an aryl group, an aralkyl group, an amino group, an acyl group, or an acylamino group, and $R^1$ to $R^5$ may be bonded to one another to form a ring;

m and n are an integer and m+n is an integer of 1 to 12;

one or more of $R^1$ to $R^5$ in a molecule are present as a carboxyl group or a hydroxyl group;

A is a carboxyl group or a hydroxyl group;

$R^6$ is an alkyl group, an alkenyl group, an aryl group, an aralkyl group, an amino group, an acyl group, or an acylamino group;

HA represents a structure obtained by removing m3+n3+p3 number of hydrogen atoms from a pyridine ring; and n3 is an integer of 1 to 4 and m3 is an integer of 0 to 5, and p3 is an integer of 1 to 4, wherein the content of the acid is 0.05 mass% or more and 20 mass% or less, the content of the mercapto compound is 0.01 mass% or more and 10 mass% or less, and a content ratio in terms of mass ratio between the content of the mercapto compound and the content of the acid is from 0.3 to 500.

40. The removal method according to claim 39, wherein one or more of $R^1$ to $R^5$ in a molecule are present as a carboxyl group.

41. A removal method for removing an oxide of a Group III-V element, comprising:

applying a treatment liquid containing an acid and a mercapto compound to an oxide of a Group III-V element to remove the oxide of a Group III-V element, wherein the treatment is carried out under a condition that light of 500 nm or less is blocked.

42. A removal method for removing an oxide of a Group III-V element, comprising:

applying a treatment liquid containing an acid and a mercapto compound to an oxide of a Group III-V element to remove the oxide of a Group III-V element, wherein the mercapto compound has at least one of a carboxyl group or a hydroxyl group, and a thiol group, the content of the acid is 0.05 mass% or more and 20 mass% or less, the content of the mercapto compound is 0.01 mass% or more and 10 mass% or less, and a content ratio in terms of mass ratio between the content of the mercapto compound and the content of the acid is from 0.3 to 500.

43. The removal method according to claim 42, wherein the mercapto compound has a carboxyl group and a thiol group.

44. A removal method for removing an oxide of a Group III-V element, comprising:

applying a treatment liquid containing an acid and a mercapto compound to an oxide of a Group III-V element to remove the oxide of a Group III-V element, wherein the mercapto compound is represented by the following Formula (1) or (4)

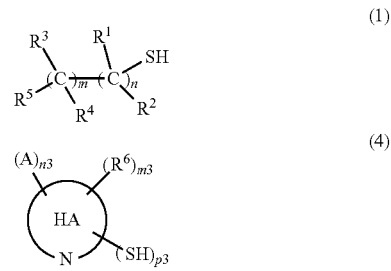

where $R^1$ to $R^5$ are each independently a hydrogen atom, a thiol group, a hydroxyl group, a carboxyl group, an alkyl group, an alkenyl group, an aryl group, an aralkyl group, an amino group, an acyl group, or an acylamino group, and $R^1$ to $R^5$ may be bonded to one another to form a ring;

m and n are an integer and m+n is an integer of 1 to 12;

one or more of $R^1$ to $R^5$ in a molecule are present as a carboxyl group or a hydroxyl group;

A is a carboxyl group or a hydroxyl group;

$R^6$ is an alkyl group, an alkenyl group, an aryl group, an aralkyl group, an amino group, an acyl group, or an acylamino group;

HA represents a structure obtained by removing m3+n3+p3 number of hydrogen atoms from a pyridine ring; and n3 and m3 are an integer of 0 to 5, and p3 is an integer of 1 to 4;

wherein the treatment is carried out under a condition that light of 500 nm or less is blocked.

\* \* \* \* \*